United States Patent [19]
Andrews et al.

[11] Patent Number: 6,013,468
[45] Date of Patent: *Jan. 11, 2000

[54] RNA COMPONENT OF TELOMERASE

[75] Inventors: William H. Andrews, Richmond, Calif.; Ariel Athena Avilion, Shoreham, N.Y.; Junli Feng, San Carlos; Walter Funk, Union City, both of Calif.; Carol Greider, Huntington; Maria Antonia Blasco Marhuenda, Mill Neck, both of N.Y.; Bryant Villeponteau, San Carlos, Calif.

[73] Assignee: Cold Spring Harbor Laboratory, Cold Spring Harbor, N.Y.

[ * ] Notice: This patent is subject to a terminal disclaimer.

[21] Appl. No.: 08/520,550

[22] Filed: Aug. 29, 1995

Related U.S. Application Data

[63] Continuation of application No. 08/387,524, Feb. 13, 1995, abandoned, which is a continuation-in-part of application No. 08/330,123, Oct. 27, 1994, Pat. No. 5,583,016, which is a continuation-in-part of application No. 08/272,102, Jul. 7, 1994, abandoned.

[51] Int. Cl.$^7$ .................................................. C07H 21/04
[52] U.S. Cl. ..................... 435/69.1; 435/240.1; 435/243; 435/320.1; 435/455; 435/471; 435/476; 536/23.1; 536/24.3; 536/24.31
[58] Field of Search ............................. 435/69.1, 240.1, 435/243, 320.1, 455, 471, 476; 514/44; 536/22.1, 23.1, 24.3, 24.31; 935/2, 3, 22, 66

[56] References Cited

U.S. PATENT DOCUMENTS 5,876,979   3/1999   Andrews et al. ...................... 435/91.3

FOREIGN PATENT DOCUMENTS

| 0666313A2 | 1/1995 | European Pat. Off. . |
| 93/23572 | 11/1993 | WIPO . |
| 95/13381 | 5/1995 | WIPO . |
| 95/13382 | 5/1995 | WIPO . |
| 95/13383 | 5/1995 | WIPO . |

OTHER PUBLICATIONS

Shippen–Lentz and Blackburn, "Functional Evidence for an RNA Template in Telomerase," *Science*, 247:546–552 (1990).
Morin, Gregg, B., "The Human Telomere Terminal Transferase Enzyme Is a Ribonucleoprotein That Synthesizes TTAGGG Repeats," *Cell*, 59:521–529 (1989).
Romero and Blackburn, "A Conserved Secondary Structure for Telomerase RNA," *Cell*, 67:343–353 (1991).
Singer and Gottschling, "TLC1: Template RNA Component of *Saccharomyces cerevisiae*," *Science*, 266:404–409 (1994).
Counter, Christopher M., et al., "Telomere Shortening Associated With Chromosome Instability Is Arrested in Immortal Cells Which Express Telomerase Activity," *EMBO*, 11(5) :1921–1929 (1992).
Collins and Greider, "Tetrahymena Telomerase Catalyzes Nucleolytic Cleavage and Nonprocessive Elongation," *Genes & Development*, 7:1364–1376 (1993).
Greider, Carol W., "Mammalian Telomere Dynamics: Healing, Fragmentation Shortening and Stabilization," *Current Opinion in Genetics and Development*, 4:203–211 (1994).
Greider and Blackburn, "The Telomere Terminal Transferase of Tetrahymena Is a Ribonucleoprotein Enzyme with Kinds Two of Primer Specificity,"*Cell*, 51:887–898 (1987).
Greider and Blackburn, "A Telomeric Sequence in the RNA of Tetrahymena Telomerase Required for Telomere Repeat Synthesis," *Nature*, 337(6205) :331–337 (1989).
Lingner, Joachin, et al., "Telomerase RNAs of Different Ciliated Have a Common Secondary Structure and a Permuted Template," *Genes & Development*, 8:1984–1998 (1994).
Greider and Blackburn, "Identification of a Specific Telomere Terminal Transferase Activity in Tetrahymena Extracts," *Cell*, 43:405–413 (1985).
Counter, Christopher M., et al., "Telomerase Activity in Human Ovarian Carcinoma," *Proc. Natl. Acad. Sci.*, 91:2900–2904 (1994).
Harley, Calvin B, et al., "Telomeres Shorten During Ageing of Human Fibroblasts," *Nature*, 345 (6274) :458–460 (1990).
Prowse, Karen, et al., "Identification of a Nonprocessive Telomerase Activity From Mouse Cells, " *Proc. Natl. Acad. Sci.*, 90:1493–1497 (1993).
Autexier and Greider, "Functional Reconstitution of Wild- –type and Mutant Tetrahymena Telomerase," *Genes & Development*, 8:563–575 (1994).
Mantell and Greider, "Telomerase Activity in Germline and Embryonic Cells of Xenopus," *The EMBO Journal*, 13 (13) :3211–3217 (1994).
Allsopp, Richard C., et al., "Telomere Length Predicts Replicative Capacity of Human Fibroblasts," *Proc. Natl. Acad. Sci.*, 89:10114–10118 (1992).
Greider, Carol, "Telomeres, Telomerase and Senescence," *BioEssays*, 12(8) :363–369 (1990).
Collins, Kathleen, et al., "Purification of Tetrahymena Telomerase and Cloning of Genes Encoding the Two Protein Components of the Enzyme," *Cell*, 81:677–686 (1995).
Feng, Junli, et al., "The RNA Component of Human Telomerase," *Science*, 269:1236–1241 (1995).
Blackburn, E.H., "Telomerases," *Annun. Rev. Biochem.*, 61:113–129 (1992).
Morin, G.B., "Recognition of a Chromosome Truncation Site Associated with α–thalassaemia by Human Telomerase," *Nature*, 353:454–456 (1991).
Harley, C.B., "Telomere Loss: Mitotic Clock or Genetic Time Bomb?," *Mutation Research*, 256:271–282 (1991).

(List continued on next page.)

*Primary Examiner*—Kenneth R. Horlick
*Attorney, Agent, or Firm*—Hamilton, Brook, Smith & Reynolds, P.C.

[57] ABSTRACT

Nucleic acids comprising the RNA component of a mammalian telomerase are useful as pharmaceutical, therapeutic, and diagnostic reagents.

31 Claims, 12 Drawing Sheets

OTHER PUBLICATIONS

Yu, Guo–Liang, et al., "In Vivo Alteration of Telomere Sequences and Senescence Caused by Mutated *Tetrahymena* Telomerase and Cloning of Genes Encoding the Two Protein Components of the Enzyme," *Nature* 344:126–132 (1990).

Blasco, M.A., et al., "Functional Characterizaton and Developmental Regulation of Mouse *Telomerase* RNA," *Science*, 269:1267–1270 (1995).

Harrington, L.A., "Characterization and Purification of Tetrahymena Telomerase," A Ph.D. Thesis presented at the State University of New York at Stony Brook, pp. 112–194 and 201–205 (Dec. 1993).

Strahl, C. et al., "The Effects of Nucleoside Analogs on Telomerase and Telomeres in Tetrahymena," *Nucleic Acids Research* 22(6):893–900 (Mar. 25, 1994).

Blackburn, E.H., "Structure and Function of Telomeres, "*Nature* 350: 569–573 (Apr. 18, 1991).

Harley, Calvin B., et al., "Human Telomerase Inhibition and Cancer," *Proceedings of the American Association for Cancer Research,* 36:670–672 (1995).

Human Telomerase RNA Component Gene

```
                                                         50
GATCAGTTAGAAAGTTACTAGTCCACATATAAAGTGCCAAGTCTTGTACT
                                                        100
CAAGATTATAAGCAATAGGAATTTAAAAAAGAAATTATGAAAACTGACA
                                                        150
AGATTTAGTGCCTACTTAGATATGAAGGGGAAGAAGGGTTTGAGATAAT
                                                        200
GTGGGATGCTAAGAGAATGGTGGTAGTGTTGACATATAACTCAAAGCATT
                                                        250
TAGCATCTACTCTATGTAAGGTACTGTGCTAAGTGCAATAGTGCTAAAAA
                                                        300
CAGGAGTCAGATTCTGTCCGTAAAAACTTTACAACCTGGCAGATGCTAT
                                                        350
GAAAGAAAAGGGGATGGGAGAGAGAAGGAGGGAGAGAGATGGAGAGG
                                                        400
GAGATATTTTACTTTTCTTTCAGATCGAGGACCGACAGCGACAACTCCAC
                                                        450
GGAGTTTATCTAACTGAATACGAGTAAAACTTTTAAGATCATCCTGTCAT
                                                        500
TTATATGTAAAACTGCACTATACTGGCCATTATAAAATTCGCGGCCGGG
                                                        550
TGCGGTGGCTCATACCTGTAATCCCAGCACTTTGGGAGGCCGAAGCGGGT
                                                        600
GGATCACTTGAGCCCTGGCGTTCGAGACCAGCCTGGGCAACATGGTGAAA
                                                        650
CCCCCGTCTCTACTAAAAACACAAAAACTAGCTGGGCGTGGTGGCAGGCG
                                                        700
CCTGTAATCCCAGCTACTCAGGAGGCTGAGACACGAGAATCGCTTGAACC
                                                        750
CGGGAGCAGAGGTTGCAGTGAGCCGAGATCACGCCACTAGACTCCATCCA
                                                        800
GCCTGGGCGAAAGAGCAAGACTCCGTCTCAAAAAAAAAAATCGTTACAAT
                                                        850
TTATGGTGGATTACTCCCCTCTTTTTACCTCATCAAGACACAGCACTACT
                                                        900
TTAAAGCAAAGTCAATGATTGAAACGCCTTTCTTTCCTAATAAAAGGGAG
                                                        950
ATTCAGTCCTTAAGATTAATAATGTAGTAGTTACACTTGATTAAAGCCAT
                                                       1000
CCTCTGCTCAAGGAGAGGCTGGAGAAGGCATTCTAAGGAGAAGGGGGCAG
                                                       1050
GGTAGGAACTCGGACGCATCCCACTGAGCCGAGACAAGATTCTGCTGTAG
                                                       1100
TCAGTGCTGCCTGGGAATCTATTTTCACAAAGTTCTCCAAAAAATGTGAT
                                                       1150
GATCAAAACTAGGAATTAGTGTTCTGTGTCTTAGGCCCTAAAATCTTCCT
                                                       1200
GTGAATTCCATTTTTAAGGTAGTCGAGGTGAACCGCGTCTGGTCTGCAGA
                                                       1250
GGATAGAAAAAGGCCCTCTGATACCTCAAGTTAGTTTCACCTTTAAAGA
```

FIG. 1A

```
                                                          1300
AGGTCGGAAGTAAAGACGCAAAGCCTTTCCCGGACGTGCGGAAGGGCAAC
                                                          1350
GTCCTTCCTCATGGCCGGAAATGGAACTTTAATTTCCCGTTCCCCCCAAC
                                                          1400
CAGCCCGCCCGAGAGAGTGACTCTCACGAGAGCCGCGAGAGTCAGCTTGG
                                                          1450
CCAATCCGTGCGGTCGGCGGCCGCTCCCTTTATAAGCCGACTCGCCCGGC
                                                          1500
AGCGCACCGGGTTGCGGAGGGAGGGTGGGCCTGGGAGGGGTGGTGGCCAT
                                                          1550
TTTTTGTCTAACCCTAACTGAGAAGGGCGTAGGCGCCGTGCTTTTGCTCC
                                                          1600
CCGCGCGCTGTTTTTCTCGCTGACTTTCAGCGGGCGGAAAAGCCTCGGCC
                                                          1650
TGCCGCCTTCCACCGTTCATTCTAGAGCAAACAAAAAATGTCAGCTGCTG
                                                          1700
GCCCGTTCGCCCCTCCCGGGACCTGCGGCGGGTCGCTGCCCAGCCCCCGA
                                                          1750
ACCCCGCCTGGAGGCCGCGGTCGGCCGGGGCTTCTCCGGAGGCACCCACT
                                                          1800
GCCACCGCGAAGAGTTGGGCTCTGTCAGCCGCGGGTCTCTCGGGGGCGAG
                                                          1850
GGCGAGGTTCACCGTTTCAGGCCGCAGGAAGAGGAACGGAGCGAGTCCCG
                                                          1900
CGCGCGGCGCGATTCCCTGAGCTATGGGACGTGCACCCAGGACTCGGCTC
                                                          1950
ACACATGCAGTTCGCTTTCCTGTTGGTGGGGGGAACGCCGATCGTGCGCA
                                                          2000
TCCGTCACCCCTCGCCGGCAGTGGGGGCTTGTGAACCCCCAAACCTGACT
                                                          2050
GACTGGGCCAGTGTGCTGCAAATTGGCAGGAGACGTGAAGGCACCTCCAA
                                                          2100
AGTCGGCCAAAATGAATGGGCAGTGAGCCGGGGTTGCCTGGAGCCGTTCC
                                                          2150
TGCGTGGGTTCTCCCGTCTTCCGCTTTTTGTTGCCTTTTATGGTTGTATT
                                                          2200
ACAACTTAGTTCCTGCTCTGCAGATTTTGTTGAGGTTTTTGCTTCTCCCA
                                                          2250
AGGTAGATCTCGACCAGTCCCTCAACGGGGTGTGGGGAGAACAGTCATTT
                                                          2300
TTTTTTGAGAGATCATTTAACATTTAATGAATATTTAATTAGAAGATCTA
                                                          2350
AATGAACATTGGAAATTGTGTTCCTTTAATGGTCATCGGTTTATGCCAGA
                                                          2400
GGTTAGAAGTTTCTTTTTTGAAAAATTAGACCTTGGCGATGACCTTGAGC
                          2425
AGTAGGATATAACCCCCACAAGCTT
```

FIG. 1B

Human Telomerase RNA component sequence

```
                                                                    50
GGGUUGCGGAGGGAGGGUGGGCCUGGGAGGGGUGGUGGCCAUUUUUUGUC
                                                                    100
UAACCCUAACUGAGAAGGGCGUAGGCGCCGUGCUUUUGCUCCCCGCGCGC
                                                                    150
UGUUUUUCUCGCUGACUUUCAGCGGGCGGAAAAGCCUCGGCCUGCCGCCU
                                                                    200
UCCACCGUUCAUUCUAGAGCAAACAAAAAAUGUCAGCUGCUGGCCCGUUC
                                                                    250
GCCCCUCCCGGGACCUGCGGCGGGUCGCUGCCCAGCCCCCGAACCCCGCC
                                                                    300
UGGAGGCCGCGGUCGGCCGGGGCUUCUCCGGAGGCACCCACUGCCACCGC
                                                                    350
GAAGAGUUGGGCUCUGUCAGCCGCGGGUCUCUCGGGGGCGAGGGCGAGGU
                                                                    400
UCACCGUUUCAGGCCGCAGGAAGAGGAACGGAGCGAGUCCCGCGCGCGGC
                                                                    450
GCGAUUCCCUGAGCUAUGGGACGUGCACCCAGGACUCGGCUCACACAUGC
                                                                    500
AGUUCGCUUUCCUGUUGGUGGGGGGAACGCCGAUCGUGCGCAUCCGUCAC
                                                                    550
CCCUCGCCGGCAGUGGGGGCUUGUGAACCCCCAAACCUGACUGACUGGGC
        559
CAGUGUGCU
```

FIG. 2

Mouse Telomerase RNA component Gene

```
                                              50
TTTTTTTTTTCCTCGTAATCTTTTTTTTTGTTTTAAACACTGGAACTTGA
                                             100
TGTCTGGAGGACGGAGTCGGAGGATGTTCGACCCTAATATCCGAGCCCAG
                                             150
TCGATGGGAACTTTAAGAAAAGAAAGACCTTGAGTCATGGACCAACCGG
                                             200
TACGTGAGTGTTCTCTAGGCGGACGGAAGACAGTTTAAGACCTTAATTTC
                                             250
TAAACGCGGTGAAAAGGGGTGAAGGTGGGGCCGACACCCTCACCTGACC
                                             300
CAACTTCCACCTTAAAAAAAAAAAAAAAAAAATCACTTTTTTCCCCCCTA
                                             350
ACCTTTATAGGGGATGAAATATCCTACTTTCAACTCTAGTATATTTCAGA
                                             400
AACCAAGCCTCAGAGATGTGCGTGCGTGCGTGTGTGTGTGTATGTGTG
                                             450
TGTGTCTCACAGCAAGAAACAGATTTTATTATTTATTTTTATTTATTTA
                                             500
TTTTTTGCAAGTGACTGGCTAGGAAGAGTGGGGAAGCGGGAGGACAAATG
                                             550
GGGAAGAGGGAGCATTTCCGCAAGTGCTGGGCTCGACCAATCAGCGCGAG
                                             600
CCATGGGGTATTTAAGGTCGAGGGCGGCTAGGCCTCGGCACCTAACCCTG
                                             650
ATTTTCATTAGCTGTGGGTTCTGGTCTTTTGTTCTCCGCCCGCTGTTTTT
                                             700
CTCGCTGACTTCCAGCGGGCCAGGAAAGTCCAGACCTGCAGCGGGCCACC
                                             750
CGGCGTTCCCGAGCCTCAAAAACAAACGTCAGCGCAGGAGCTCCAGGTTC
                                             800
GCCGGGAGCTCCGCGCGCCGGGCCGCCAGTCCCGTACCCGCCTACAGGCC
                                             850
GCGGCGCTGGGGTCTTAGGACTCCGCTGCCGCCGCGAAGAGCTGCGCTCT
                                             900
GTCAGCCGCGGGCGCGCGGGGCGTGGGGCAGGCGGGCGAGCGCGCGAGGA
                                             1000
CACCGGACTCGGTTCTCACACCCCATTCCCGCTGGGGAAATGCCCCGCTG
                                             1050
CAGGGCGGGCCGCTAGAACCTGCGACTCTGGGGAAAGGGGCTTCGGTGTG
                                             1100
AGACGGTCGCCAGCCAAAGGGTATATATCGCCCTCACGCCCCGTCCCCCT
                                             1150
CCACTTTTGTCTAATACTCCTGTTTCTGTTGTGCAGATTTTGCAGGCGTT
                                             1200
TCGCTGGCTCTGCCTGAACGAGCTATCAGCCATGTGGTCCTTGGGGGTGG
                                             1250
GGGTGGGGATGGGTTGTGTAGTGCTGGGAATGAACCTAGTTTCTAAGTTC
       1259
TCTATCAAC
```

FIG. 3

Mouse Telomerase RNA component sequence

```
                                                              50
CUCGACCAAUCAGCGCGAGCCAUGGGGUAUUUAAGGUCGAGGGCGGCUAG
                                                             100
GCCUCGGCACCUAACCCUGAUUUUCAUUAGCUGUGGGUUCUGGUCUUUUG
                                                             150
UUCUCCGCCCGCUGUUUUUCUCGCUGACUUCCAGCGGGCCAGGAAAGUCC
                                                             200
AGACCUGCAGCGGGCCACCCGGCGUUCCCGAGCCUCAAAAACAAACGUCA
                                                             250
GCGCAGGAGCUCCAGGUUCGCCGGGAGCUCCGCGCGCCGGGCCGCCAGUC
                                                             300
CCGUACCCGCCUACAGGCCGCGGCGCUGGGGUCUUAGGACUCCGCUGCCG
                                                             350
CCGCGAAGAGCUGCGCUCUGUCAGCCGCGGGCGCGCGGGGCGUGGGGCAG
                                                             400
GCGGGCGAGCGCGCGAGGACAGGAAUGGAACUGGUCCGUGUUCGGUGUCU
                                                             450
UACUGAGCUGUGGGAAGUGCACCGGACUCGGUUCUCACACCCCAUUCCCG
                                                             500
CUGGGGAAAUGCCCCGCUGCAGGGCGGGCCGCUAGAACCUGCGACUCUGG
                                          534
GGAAAGGGGCUUCGGUGUGAGACGGUAGCCAGCC
```

FIG. 4

COMPARISON OF MOUSE AND HUMAN RNA COMPONENTS

```
             ┌─► +1 Mouse      ┌─► +1 Human
Mouse CUCGACCAAUCAGCGCGCGCCAUGG-GGUAUUUAAGGUC---GAGGGCGG           46
Human ---------------GGGUUGCGGAGGGAGGGUGGCCUGGGAGGGGUG             34

CUAGGC-CUCGGCA▒▒▒▒▒▒▒▒GAUUUUCAUUAGCUGUGGGUUCUGGUC            95
      GUGGCCAUUUUUUGU▒▒▒▒▒▒▒▒UGAGAAGGGC-GUAGGCGCCGUGC              83

UUUUGUUCUCCGCCCGCUGUUUUUCUCGCUGACUUCCAGCGGGCCAGGAA            145
      UUUUGCUCCCCGCGCGCUGUUUUUCUCGCUGACUUUCAGCGGGC-GGAAA            132

AGUCCAGACCUGCAGCGGGCCACCCGGCGUUCCCGAGCCUCAAAAACAAA            195
      AGCCUCGGCCUGCCGCCUUCCACCGUUCAUUCUAGAGC--AAACAAAAAA            180

CGUCAGC-GCAGGAGCUCCAGGUUCGCCGGGAGCUCCGCGGCGCCGGGCC            244
      UGUCAGCUGCUGGCCCGUUCGCCCGUCCCGG-GACCUGCGGCGGGUCGCU            229

GCCCAG-UCCCGUACCC-GCCUACAGGCCGCGGCCGGCCUGGG-GUCUUA            291
      GCCCAGCCCCCGAACCCCGCCUGGAGGCCGCGGUCGGCCGGGGCUUCUCC            279

GGA--C-UCCGCUGCCGCCGCGAAGAGCUCCGCCUCUGUCAGCCGCGGG-            337
      GGAGGCACCCACUGCCACCGCGAAGAG-UUGGGCUCUGUCAGCCGCGGGU            328

CGCGCGGGGGCUGGGGCAGG----CCGGGCGAGCGCCGCGAGGACAGGA             383
      CUCUCGGGGGCGAGGGCGAGGUUCACCGUUUCAG-GCCGCAGGAAGAGGA            377

AUGGAACUGGUCCCCGUGUUCGGUGU-CUUACCUGAGCUGUGGGAAGUGC            432
      ACGGAGCGAGU-CCCGCGCGCGGCGCGAUUCCCUGAGCUAUGGGACGUGC            426

ACCCGGAACUCGGUUCUCACA---A-CCCCCAUUCCCGCUGGGGAAAUGC            478
      ACCCAGGACUCGGCUCACACAUGCAGUUCGCUUUCCUGUUGGUG-GGGGG            475

CCCGCUG-CAGGGCG-GGCCGCUAGAACCUG-CGACUCUGGGGAAAGGGG            525
      AACGCCGAUCGUGCGCAUCCGUCACCCCUCGCCGGCAGUGGGGGCUUGUG            525

---CUUC-GGUGUGA--GAC--GG-UAGCCAGCCAAAGGGUAUAUAUCGC            566
      AACCCCCAAACCUGACUGACUGGGCCAGUGUGCU---------------            559

CCUCACGCCCCGUC                                                 580
      --------------                                                 559
```

FIG. 5

Partial Sequence of the Rat Telomerase RNA

```
                                                              50
UCAGCGGGCCUGAAAGUUCAGACCUGCAGCGGGUCACGCGCAUUCUGAAC
                                                             100
CUCAAAAAAUGUCAGCGUAGAGCUCUGGUGCCAGAGCUCGNCGGCGCUGG
                                                             150
GCCGCCCAGCCCGGUACCCNGCCUGGAGCCGCGGACGGCCUGGGGUCUUA
                                                             200
GAACCGUGCCGCCGUGAAGAGCUAGUUUCUGUUAGCUACGGGGCACCGGG
    10                                                       250
CGCUGGGGUCAGGCCGGGAGAGCGCCGCAAGGACAGUAACGGAACUGGUC

CCUGAGUUCGGUGGCUUUC                                          269
```

FIG. 7

Human Telomerase RNA Component Gene

```
GGGTTGCGGA GGGTGGGCCT GGGAGGGGTG GTGGCCATTT TTTGTCTAAC   50
CCTAACTGAG AAGGGCGTAG GCGCCGTGCT TTTGCTCCCC GCGCGCTGTT  100
TTTCTCGCTG ACTTTCAGCG GGCGGAAAAG CCTCGGCCTG CCGCCTTCCA  150
CCGTTCATTC TAGAGCAAAC AAAAAATGTC AGCTGCTGGC CCGTTCGCCT  200
CCCGGGGACC TGCGGCGGGT CGCCTGCCCA GCCCCCGAAC CCGCCTGGA   250
GGCCGCGGTC GGCCCGGGGC TTCTCCGGAG GCACCCACTG CCACCGCGAA  300
GAGTTGGGCT CTGTCAGCCG CGGGTCTCTC GGGGGCGAGG GCGAGGTTCA  350
CCGTTTCAGG CCGCAGGAAG AGGAACGGAG CGAGTCCCCG CGCGCGGCGC  400
GATTCCCTGA GCTGTGGGAC GTGCACCCAG GACTCGGCTC ACACATGCAG  450
TTCGCTTTCC TGTTGGTGGG GGGAACGCCG ATCGTGCGCA TCCGTCACCC  500
CTCGCCGGCA GTGGGGGCTT GTGAACCCCC AAACCTGACT GACTGGGCCA  550
GTGTGCTGCA AATTGGCAGG AGACGTGAAG GCACCTCCAA AGTCGGCCAA  600
AATGAATGGG CAGTGAGCCG GGGTTGCCTG GAGCCGTTCC TGCGTGGGTT  650
CTCCCGTCTT CCGCTTTTTG TTGCCTTTTA TGGTTGTATT ACAACTTAGT  700
TCCTGCTCTG CAGATTTTGT TGAGGTTTTT GCTTCTCCCA AGGTAGATCT  750
CGACCAGTCC CTCAACGGGG TGTGGGGAGA ACAGTCATTT TTTTTTGAGA  800
GATCATTTAA CATTTAATGA ATATTTAATT AGAAGATCTA AATGAACATT  850
GGAAATTGTG TTCCTTTAAT GGTCATCGGT TTATGCCAGA GGTTAGAAGT  900
TTCTTTTTTG AAAAATTAGA CCTTGGCGAT GACCTTGAGC AGTAGGATAT  950
AACCCCCACA AGCTT                                        965
```

FIG. 8

Human Telomerase RNA Component

```
GGGUUGCGGA GGGUGGGCCU GGGAGGGGUG GUGGCCAUUU UUUGUCUAAC    50
CCUAACUGAG AAGGGCGUAG GCGCCGUGCU UUUGCUCCCC GCGCGCUGUU   100
UUUCUCGCUG ACUUUCAGCG GGCGGAAAAG CCUCGGCCUG CCGCCUUCCA   150
CCGUUCAUUC UAGAGCAAAC AAAAAAUGUC AGCUGCUGGC CCGUUCGCCU   200
CCCGGGGACC UGCGGCGGGU CGCCUGCCCA GCCCCGAAC  CCCGCCUGGA   250
GGCCGCGGUC GGCCCGGGGC UUCUCCGGAG GCACCCACUG CCACCGCGAA   300
GAGUUGGGCU CUGUCAGCCG CGGGUCUCUC GGGGGCGAGG GCGAGGUUCA   350
CCGUUUCAGG CCGCAGGAAG AGGAACGGAG CGAGUCCCCG CGCGCGGCGC   400
GAUUCCCUGA GCUGUGGGAC GUGCACCCAG GACUCGGCUC ACACAUGC    448
```

FIG. 9

Mouse Telomerase RNA Component Gene

```
CTCGACCAAT CAGCGCGCGC CATGGGGTAT TTAAGGTCGA GGGCGGCTAG    50
GCCTCGGCAC CTAACCCTGA TTTTCATTAG CTGTGGGTTC TGGTCTTTTG   100
TTCTCCGCCC GCTGTTTTTC TCGCTGACTT CCAGCGGGCC AGGAAAGTCC   150
AGACCTGCAG CGGGCCACCC GGCGTTCCCG AGCCTCAAAA ACAAACGTCA   200
GCGCAGGAGC TCCAGGTTCG CCGGGAGCTC CGCGGCGCCG GCCGCCCAG    250
TCCCGTACCC GCCTACAGGC CGCGGCCGGC CTGGGGTCTT AGGACTCCGC   300
TGCCGCCGCG AAGAGCTCCG CCTCTGTCAG CCGCGGGCGC GCGGGGGCTG   350
GGGCCAGGCC GGGCGAGCGC CGCGAGGACA GGAATGGAAC TGGTCCCCGT   400
GTTCGGTGTC TTACCTGAGC TGTGGGAAGT GCACCCGGAA CTCGGTTCTC   450
ACAACCCCCA TTCCCGCTGG GGAAATGCCC CGCTGCAGGG CGGGCCGCTA   500
GAACCTGCGA CTCTGGGGAA AGGGGCTTCG GTGTGAGACG GTAGCCAGCC   550
AAAGGGTATA                                              560
```

FIG. 10

Mouse Telomerase RNA Component

```
GGGUAUUUAA GGUCGAGGGC GGCUAGGCCU CGGCACCUAA CCCUGAUUUU    50
CAUUAGCUGU GGGUUCUGGU CUUUUGUUCU CCGCCCGCUG UUUUUCUCGC   100
UGACUUCCAG CGGGCCAGGA AAGUCCAGAC CUGCAGCGGG CCACCCGGCG   150
UUCCCGAGCC UCAAAAACAA ACGUCAGCGC AGGAGCUCCA GGUUCGCCGG   200
GAGCUCCGCG GCGCCGGGCC GCCCAGUCCC GUACCCGCCU ACAGGCCGCG   250
GCCGGCCUGG GGUCUUAGGA CUCCGCUGCC GCCGCGAAGA GCUCCGCCUC   300
UGUCAGCCGC GGGCGCGCGG GGGCUGGGGC CAGGCCGGGC GAGCGCCGCG   350
AGGACAGGAA UGGAACUGGU CCCCGUGUUC GGUGUCUUAC CUGAGCUGUG   400
GGAAGUGCAC CCGGAACUCG GUUCUCACA                          429
```

FIG. 11

RNA COMPONENT OF TELOMERASE

RELATED APPLICATIONS

This application is a continuation of U.S. patent application Ser. No. 08/387,524, filed Feb. 13, 1995, which is a continuation-in-part of U.S. patent application Ser. No. 08/330,123, filed Oct. 27, 1994, U.S. Pat. No. 5,583,016, which is a continuation-in-part of U.S. patent application Ser. No. 08/272,102, filed Jul. 7, 1994, abandoned. The teachings of all of these applications are expressly incorporated herein by reference.

GOVERNMENT SUPPORT

The invention described herein was made in whole or in part with government support under Grants Number NIH 5RO1 AG09383-04 and NIH 5RO1 GM43080-05 awarded by the National Institutes of Health. The United States Government has certain rights in the invention.

BACKGROUND OF THE INVENTION

The DNA at the ends or telomeres of the chromosomes of eukaryotes usually consists of tandemly repeated simple sequences. Telomerase is a ribonucleoprotein enzyme that synthesizes one strand of the telomeric DNA using as a template a sequence contained within the RNA component of the enzyme. See Blackburn, E. H. (1992) *Annu. Rev. Biochem.* 61:113–129, incorporated herein by reference.

The RNA component of a mammalian telomerase has not been reported in the scientific literature to date, although, human and mouse telomerases are known to synthesize telomeric repeat units with the sequence 5'-TTAGGG-3'. See Morin, G. B (1989) *Cell* 59:521–529; Morin, G. B. (1991) *Nature* 353:454–456; Prowse, et al. (1993) *PNAS* 90:1493–1497, incorporated herein by reference. This knowledge has not been sufficient to enable the isolation and identification of the remainder of the nucleotide sequence of the RNA component of either of these telomerases. The RNA component of the telomerase enzymes of *Saccharomyces cerevisiae,* certain species of Tetrahymena, as well as that of other ciliates, such as Oxytricha, Euplotes and Glaucoma, has been sequenced and reported in the scientific literature. See Singer, M. S. and D. E. Gottschling (1994) *Science* 266:404–409; Lingner et al. (1994) *Genes & Development* 8:1984–1988; Greider, C. W and E. H. Blackburn (1989) *Nature* 337:331–337; Romero, D. P. and E. H. Blackburn (1991) *Cell* 67:343–353; Shippen-Lentz, D. and E. H. Blackburn (1990) *Science* 247:546–552. The teachings of each of these references are incorporated herein by reference. The telomerase enzymes of these ciliates synthesize telomeric repeat units distinct from that in mammals.

There is a great need for more information about mammalian telomerase. Despite the seemingly simple nature of the repeat units of telomeric DNA, scientists have long known that telomeres have an important biological role in maintaining chromosome structure and function. More recently, scientists have speculated that loss of telomeric DNA may act as a trigger of cellular senescence and aging and that regulation of telomerase may have important biological implications. See Greider, C. W. (1994) *Curr. Opin. Genetics Devel.* 4:203–211; Harley, C. B. (1991) *Mutation Res.* 256:271–282; Harley, C. B. et al. (1990) *Nature* 345:458–460, incorporated herein by reference.

Methods for detecting telomerase activity, as well as for identifying compounds that regulate or affect telomerase activity, together with methods for therapy and diagnosis of cellular senescence and immortalization by controlling telomere length and telomerase activity, have also been described. See PCT patent publication No. 93/23572, published Nov. 25, 1993, incorporated herein by reference.

Significant improvements to and new opportunities for telomerase-mediated therapies and telomerase assays and screening methods could be realized if nucleic acids comprising the RNA component and/or encoding the protein components of telomerase were available in pure or isolated form and the nucleotide sequences of such nucleic acids were known.

SUMMARY OF THE INVENTION

In a first aspect, the present invention provides the RNA component of, as well as the gene for the RNA component of, human telomerase in substantially pure form, as well as nucleic acids comprising all or at least a portion of the nucleotide sequence of the RNA component of human telomerase. The present invention also provides the RNA component of, and the gene for the RNA component of, mouse telomerase in substantially pure form, as well as nucleic acids comprising all or at least a portion of the nucleotide sequence of the RNA component of mouse telomerase. The present invention further provides RNA component nucleic acids and genes encoding such RNA component nucleic acids from other species, including the RNA component of rat telomerase. The RNA components include, but are not limited to, the RNA components of mammals, such as primates. Other nucleic acids of the invention include nucleic acids with sequences complementary to the RNA component; nucleic acids with conserved nucleotide residues of RNA components; nucleic acids with sequences related to, but distinct from, nucleotide sequences of the RNA components and which interact with the RNA component or the gene for the RNA component of the protein components of human telomerase in a useful way; and nucleic acids that do not share significant sequence homology or complementarity to the RNA component or the gene for the RNA component but act on the RNA component in a desired and useful way. As described more fully below, the nucleic acids of the invention include both DNA and RNA molecules and modified analogues of either and serve a variety of purposes.

Thus, one type of nucleic acid of the invention is an antisense oligonucleotide that can be used in vivo or in vitro to inhibit the activity of a mammalian telomerase, such as human telomerase. Such oligonucleotides can block telomerase activity in a number of ways, including by preventing transcription of the telomerase gene (for instance, by triple helix formation) or by binding to the RNA component of telomerase in a manner that prevents a functional ribonucleoprotein telomerase from assembling or prevents the RNA component, once assembled into the telomerase enzyme complex, from serving as a template for telomeric DNA synthesis. Typically, and depending on mode of action, these oligonucleotides of the invention comprise a specific sequence of from about 10 to about 25 to 200 or more nucleotides that is either identical or complementary to a specific sequence of nucleotides in the RNA component of telomerase or the gene for the RNA component of telomerase.

Another type of nucleic acid of the invention is a ribozyme able to cleave specifically the RNA component of a mammalian telomerase, rendering the enzyme inactive. Yet another type of nucleic acid of the invention is a probe or primer that binds specifically to the RNA component of a mammalian telomerase and so can be used, e.g., to detect the presence of telomerase in a sample. Finally, nucleic acids of the invention include recombinant expression plasmids for producing the nucleic acids of the invention. One type of such a plasmid is a plasmid used for human gene therapy or for use in mouse, rat or other mammalian experimental models. Plasmids of the invention for human gene therapy or mammalian models come in a variety of types, including not only those that encode antisense oligonucleotides or ribozymes, but also those that drive expression of the RNA components of mammalian telomerase or a deleted or otherwise altered (mutated) version of the RNA component of human, mouse, or rat (or other species with RNA component sequences homologous to these RNA components and/or which encode a functional RNA component when combined with the appropriate telomerase protein component) telomerase or the gene for the same.

In a second aspect, the invention provides methods for treating a condition associated with the telomerase activity within a cell or group of cells by contacting the cell(s) with a therapeutically effective amount of an agent that alters telomerase activity in that cell. Such agents include the telomerase RNA component-encoding nucleic acids, triple helix-forming oligonucleotides, antisense oligonucleotides, ribozymes, and plasmids for human gene therapy or mammalian models described above. In a related aspect, the invention provides pharmaceutical compositions comprising these therapeutic agents together with a pharmaceutically acceptable carrier or salt.

In a third aspect, the invention provides diagnostic methods for determining the level, amount, or presence of the RNA component of human telomerase, mouse telomerase, telomerase, or telomerase activity in a cell, cell population, or tissue sample, or an extract of any of the foregoing. In a related aspect, the present invention provides reagents for such methods (including the primers and probes noted above), optionally packaged into kit form together with instructions for using the kit to practice the diagnostic method.

In a fourth aspect, the present invention provides recombinant telomerase preparations and methods for producing such preparations. Thus, the present invention provides a recombinant human, mouse, rat or other mammalian telomerase that comprises the protein components of the human, mouse or rat telomerase as well as the protein components of telomerase from another mammalian species with an RNA component substantially homologous to the RNA component of human, mouse, rat or other telomerase in association with a recombinant RNA component of the inventions. Such recombinant RNA component molecules of the invention include those that differ from naturally-occurring RNA component molecules by one or more base substitutions, deletions, or insertions, as well as. RNA component molecules identical to a naturally-occurring RNA component molecule that are produced in recombinant host cells. The method for producing such recombinant telomerase molecules comprises transforming a eukaryotic host cell that expresses the protein components of telomerase with a recombinant expression vector that encodes an RNA component molecule of the invention, and. culturing said host cells transformed with said vector under conditions such that the protein components and RNA component are expressed and assemble to form an active telomerase molecule capable of adding sequences (not necessarily the same sequence added by native telomerase) to telomeres of chromosomal DNA.

In a fifth aspect, the invention provides methods for purifying the protein components of human telomerase as well as the protein components of telomerase from another mammalian species with an RNA component substantially homologous to the RNA component of human telomerase. The present invention also provides methods for isolating and identifying nucleic acids encoding such protein components. In related aspects, the present invention provides purified human and mouse telomerase and purified telomerase of another mammalian species with an RNA component substantially homologous to the coding regions of the RNA components of human, mouse, rat or other mammalian telomerase, as well as purified nucleic acids that encode one or more components of such telomerase preparations. The present invention also provides pharmaceutical compositions comprising as an active ingredient the protein components of telomerase or a nucleic acid that encodes or interacts with a nucleic acid that encodes a protein component of telomerase.

In a sixth aspect, the invention provides a mammalian model system through which telomere regulation can be studied in vivo. A mouse or rat model, particularly a knock-out mouse, offers an excellent system in which the role of telomerase in aging and immortalization can be directly tested. Altered telomerase and compounds that affect the telomerase activity can be used to determine the effects of telomerase on both cell viability and organismal development.

Other features and advantages of the invention will be apparent from the following description of the drawings, preferred embodiments of the invention, the examples, and the claims.

BRIEF DESCRIPTION OF THE FIGURES

FIGS. 1A–1B are the DNA sequence (SEQ ID NO:1) encoding the human telomerase RNA component.

FIG. 2 is the RNA sequence (SEQ ID NO:2) of the human telomerase RNA component.

FIG. 3 is the DNA sequence (SEQ ID NO:3) encoding the mouse telomerase RNA component.

FIG. 4 is the RNA sequence (SEQ ID NO:4) of the mouse telomerase RNA component.

FIG. 5 is a comparison of the mouse and human ribonucleotide sequences that comprise the RNA component of telomerase. The coding region for each begins at the +1 position indicated.

FIG. 7 is a partial RNA sequence (SEQ ID NO:5) of the rat telomerase RNA component.

FIG. 8 is a later-derived DNA sequence (SEQ ID NO:44) encoding the human telomerase RNA component.

FIG. 9 is the later-derived RNA sequence (SEQ ID NO:45) of the human telomerase RNA component.

FIG. 10 is the later-derived DNA sequence (SEQ ID NO:46) encoding the mouse telomerase RNA component.

FIG. 11 is the later-derived RNA sequence (SEQ ID NO:47) of the mouse telomerase RNA component.

DETAILED DESCRIPTION OF THE INVENTION

Figure 6:
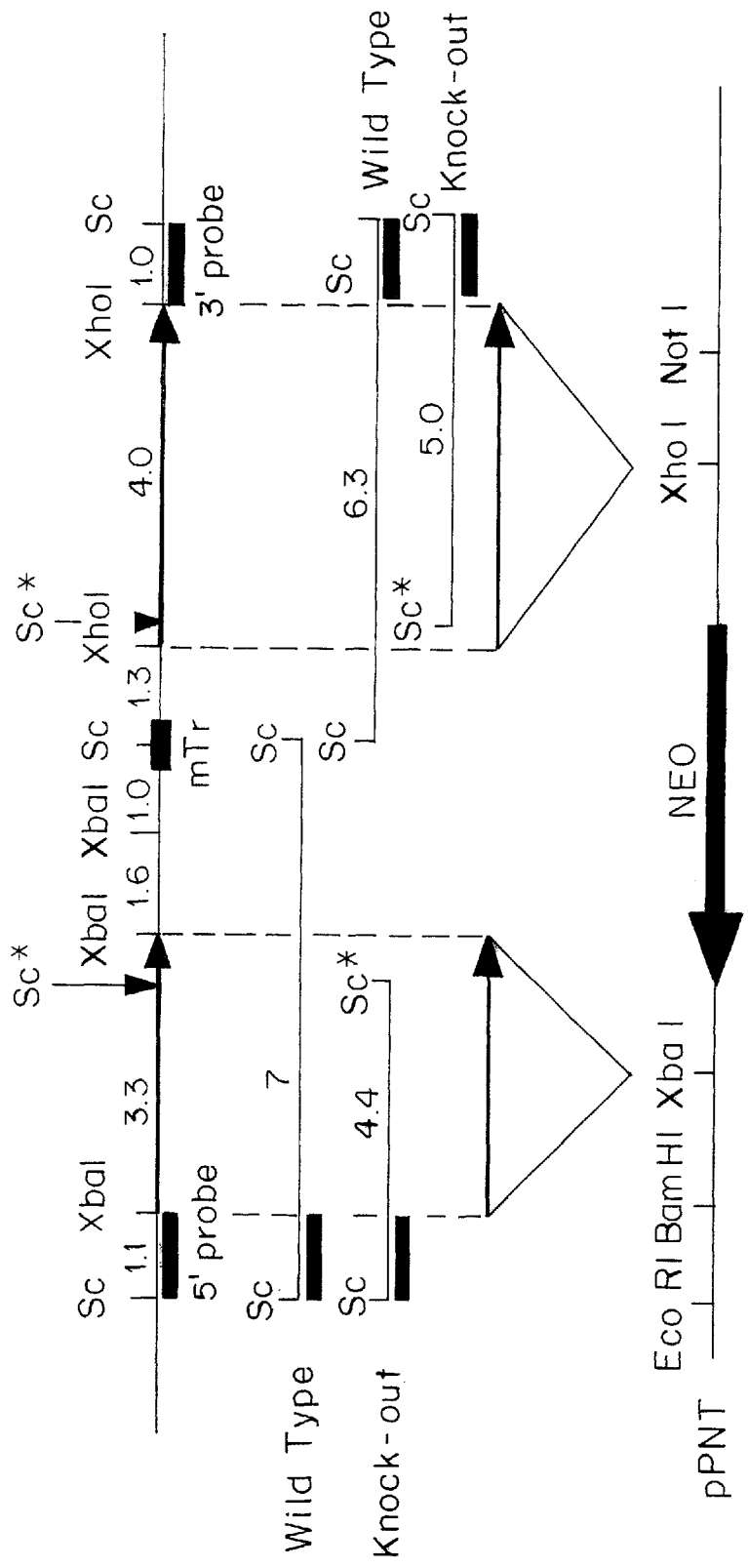
FIG. 6 is a diagram of a targeting construct for knocking out the mouse telomerase RNA component.

The present invention provides methods, reagents, and pharmaceutical compositions relating to the ribonucleoprotein mammalian telomerases. The invention in part arises out of the cloning and isolation of the RNA components of mammalian telomerases, particularly human, mouse, and rat telomerases and the genes for those RNA components. The nucleotide sequences of the RNA components of both human and mouse telomerase are shown in FIGS. 2 and 4, respectively, and the partial sequence of the rat RNA component is shown in FIG. 7. For convenience, the sequences are shown using the standard abbreviations for ribonucleotides (A is riboadenine, G is riboguanine, C is ribocytidine, and U is uridine). The DNA sequences for the human and mouse telomerase RNA genes are shown in FIGS. 1A–1B and 3, respectively.

The sequences in FIGS. 2, 4, and 7 are shown in the 5'-3' direction and are numbered for reference. The template sequence of the human RNA component (FIG. 2) is believed to be located within the region defined by nucleotides 50–60 (5'-CUAACCCUAAC-3'), which is complementary to a telomeric sequence composed of about one-and-two-thirds telomeric repeat units.

These sequences were derived from cDNA clones and from the genomic clone of the RNA components. When the RNA component is first transcribed from the corresponding human or mouse gene, at least some of the RNA transcripts produced are much longer than the ~560 and ~535 nucleotide sequences shown and in fact may comprise more than 1000 nucleotides. However, fully functional telomerase molecules can be assembled from transcripts consisting of the ~560 and ~535 nucleotide sequences shown in the figures.

The 3'-end of the RNA component in native human telomerase is believed to lie within the region defined by nucleotides 514–559 in the human sequence above; one analysis suggests that the 3'-end may be the U residue at nucleotide 538. Recombinant RNA component molecules comprising less than nucleotides 1–559 of the human sequence shown above can also be used to prepare active telomerase.

The RNA Component of Human Telomerase

The cloning of the RNA component of human telomerase required a novel method involving negative selection and cycles of positive selection, described below. Initially, however, an attempt was made to clone the RNA component using reverse transcription and a method for cloning the ends of cDNA called "5'-RACE PCR amplification". The reverse transcription reaction was initiated with a primer identical to the repeat unit in the single-strand portion of human telomeric DNA and thus complementary to a sequence believed to be present in the RNA component of human telomerase. The primer also comprised, at its 5'-end, a sequence corresponding to a restriction enzyme recognition site. However, when the cDNA produced by the reverse transcription reaction and PCR amplification was examined by gel electrophoresis and nucleotide sequence analysis of the bands of nucleic acid present in the gel, only ribosomal RNA sequences were detected. Similar problems were encountered when variations of this 5'-RACE approach were attempted using nested primers.

The successful cloning effort began with the preparation of cDNA from purified preparations of human telomerase, as well as from cell lines that have human telomerase activity and from cell lines that do not have detectable human telomerase activity. The method used to prepare the cDNA is described in detail in Example 1, below. Two negative selection steps and successive cycles of positive selection were used in conjunction with the cDNA preparations from the two human cell lines to lower the concentration of unwanted sequences and to raise the concentration of the desired RNA component sequences.

The negative selection steps involved the preparation of biotinylated PCR product from cDNA prepared from a human cell line that does not have detectable telomerase activity. The biotinylated PCR product was denatured and then rehybridized in a solution comprising a much lower concentration of non-biotinylated PCR product (100 biotinylated product:1 non-biotinylated product) from cDNA prepared from a human cell line that does have telomerase activity. Given the possibility that the telomerase negative cell line might contain some low amount of the RNA component, the hybridization step was conducted to discriminate or select against only RNA expressed abundantly in both cell lines. After hybridization to a Cot selected to allow hybridization of the most abundantly expressed RNA, the unwanted material was removed by binding to streptavidinylated magnetic particles; the supernatant remaining after particle collection contained the desired cDNA for the RNA component of human telomerase. The process for PCR amplification of cDNA is described in Example 2, below.

This material was further enriched for the desired cDNA by successive cycles of positive selection. In the positive selection step, a biotinylated probe complementary to the predicted template sequence in the RNA component of human telomerase was hybridized to PCR product from an enriched (by negative selection) sample of the PCR- amplified cDNA from a human cell line that has telomerase activity. After hybridization, the probe/target complexes were bound to avidinylated magnetic beads, which were then collected and used as a source of nucleic acid enriched in RNA component sequences in further cycles of positive selection. The positive selection process is described in more detail in Examples 3 and 4, below.

After the third cycle of positive selection, the amplification products were separated by gel electrophoresis, and sections of the gel corresponding to nucleic acids ~200 bp in size were removed. The nucleic acids were then eluted from the gel sections and amplified by PCR. The PCR amplification products were digested with restriction enzyme Not1 and then inserted by ligation into the Not1 site of plasmid pBluescriptIISK+, commercially available from Stratagene. The resulting plasmids were transformed into *E. coli* host cells, and individual colonies were isolated and used as a source of nucleic acid for further analysis and DNA sequencing. Individual colonies were grown in the wells of a 96-well microtiter plate, which was then used as a master plate, and blots of DNA from the colonies in the plate were prepared and hybridized to a probe comprising a telomeric repeat sequence and therefore complementary to the RNA component of human telomerase. A number of clones positive by this test were then analyzed by DNA sequencing and a variety of other tests.

These other tests included the following: (1) determination of whether antisense oligonucleotides complementary to the putative RNA component would inhibit telomerase activity in human cell extracts known to contain telomerase (Greider, C. W. and E. H. Blackburn (1989) supra); (2) determination of whether PCR primers specific for a putative RNA component clone sequence could be used to amplify a nucleic acid present in a telomerase sample and whether the product observed, if any, would track telomerase activity during purification of telomerase (Greider, C. W. and E. H. Blackburn (1987) supra); and (3) determination of whether PCR primers specific for a putative RNA component clone sequence could be used to amplify a nucleic acid present in greater abundance in cell extracts from cells in which telomerase activity is known to be high (i.e., tumor cells) than in cell extracts from cells known to produce no or only low amounts of telomerase activity. One clone, designated plasmid pGRN7, produced results in these tests consistent with the determination that the plasmid comprised cDNA corresponding to the RNA component of human telomerase.

Thus, antisense oligonucleotides corresponding to sequences of the putative RNA component sequence of pGRN7 exhibited inhibition of telomerase activity in vitro. Likewise, when telomerase was purified from cell extracts by a process involving (1) DEAE chromatography; (2) Sephadex S300 chromatography; and (3) either glycerol gradient, SP sepharose, or phenyl sepharose separation and fractions collected, PCR primers specific for the putative RNA component sequence of pGRN7 amplified a nucleic acid of the appropriate size, and the amount of amplification product correlated well with the amount of telomerase activity observed in the fractions collected. Finally, cell extracts from normal (no detectable telomerase activity) and cancer (telomerase activity present), as well as testis (telomerase activity present), cells showed corresponding amounts of PCR product upon reverse transcription and PCR amplification (RT-PCR) with primers specific for the putative RNA component comprised in pGRN7. The protocol for the RT-PCR is described in Examples 5 and 6, below.

The above results provided convincing evidence that the RNA component of human telomerase had been cloned. Therefore, plasmid pGRN7 was then used to isolate a genomic clone for the RNA component from a human cell line, as described in Example 7, below. The genomic clone was identified in and isolated from a genomic library of human DNA inserted into a lambda vector FIXII purchased from Stratagene. The desired clone comprising the RNA component gene sequences contained an ~15 KB insert and was designated clone 28-1. This clone has been deposited with the American Type Culture Collection and is available under the ATCC accession No. 75925. Various restriction fragments were subcloned from this phage and sequenced. The gene has also been localized to the distal end of the q arm of chromosome 3. The sequence information obtained from a SauIIIA1 restriction enzyme recognition site at one end of the ~15 kb insert to an internal HindIII restriction enzyme recognition site, which comprises all of the mature RNA component sequence as well as transcription control elements of the RNA component gene, of lambda clone 28-1 is shown in FIGS. 1A–1B using the standard deoxyribonucleotide abbreviations and depicted in the 5'-3' direction.

The RNA component sequence begins at base 1459 and ends at base 2017. A variety of transcription control elements can also be identified in the sequence. An A/T Box consensus sequence is found at nucleotides 1438–1444; PSE consensus sequences are found at nucleotides 1238–1250 as well a nucleotides 1406–1414; a CAAT Box consensus sequence is found at nucleotides 1399–1406; an SP1 consensus sequence is found at nucleotides 1354–1359; and a beta-interferon response element consensus sequence is found at nucleotides 1234–1245.

The plasmids described above that were constructed during the cloning of the RNA component of human telomerase and the gene for the RNA component are important aspects of the present invention. These plasmids can be used to produce the RNA component of, as well as the gene for, human telomerase in substantially pure form, yet another important aspect of the present invention. In addition, those of skill in the art recognize that a variety of other plasmids, as well as non-plasmid nucleic acids in substantially pure form, that comprise all or at least a portion of the nucleotide sequence of the RNA component of human telomerase are provided by the present invention.

The RNA Component of Mouse Telomerase

The cloning of the mouse RNA component of telomerase was initiated by isolating highly purified mouse telomerase fractions using five different column chromatography steps. These active fractions were highly enriched for the RNA component and provided essential ribonucleoenzyme materials for cloning procedures. The cloning procedures are described in detail in Examples 9–13, and the mouse telomerase RNA component gene is shown in FIG. 3. The RNA component sequence begins at base 531 and ends at base 1111.

The small RNAs which co-purified with telomerase were sequenced and those that had the template region CTAAC-CCTAA were identified and targeted as potential RNAs involved in telomerase elongation. The potential RNA generated while cloning the human telomerase RNA component also showed characteristics of a telomerase component. Using the genomic clone of the human RNA component, mouse genomic fragments were identified from a lambda library that hybridized to a human probe at medium stringency. Approximately five genome equivalents were screened with a probe that contained 500 bp of the human telomerase RNA gene. The positive lambda phage were restriction mapped and four were identical to each other. Two positive bands in a Pst1 digest of the clones which hybridized to the human gene were subcloned and sequenced. The sequence was 64% identical to the 550 nucleotide coding region of the human telomerase RNA indicating that this clone might be the mouse telomerase RNA gene. Outside of coding region, the sequence identity dropped to 45%. The sequence identity in the coding region of the human and putative mouse RNAs is significantly less than that found for other small RNA genes between human and mouse. The U-RNA species range from 100% identity for U6 to 85% identity for U7. The mouse and human RNase P RNA and MRP RNAs are 86% and 78% identical respectively. Thus the telomerase RNA is the least well conserved between human and mouse of any mammalian small functional RNA yet identified. This low level of sequence conservation among telomerase RNAs has also been found in the ciliates. Lingner, et al. (1994) supra; Romero, D. P. and E. H. Blackburn, (1991) supra.

The template region of the human RNA is not absolutely conserved in the mouse sequence. There are 11 nucleotides in the potential template of the human RNA CUAAC-CCUAAC while there are only 9 possible nucleotides in the mouse RNA CCUAACCCU. This change may be the cause of the decreased processivity of the mouse enzyme relative to the human enzyme. Prowse, et al. (1993) supra.

Due to the low level of sequence conservation between the human and mouse clones, several approaches were used to determine whether the mouse sequence represents the functional telomerase RNA. First, genomic Southern blots probed at high stringency identified a single band when probed with the potential coding region (data not shown). At lower stringency, several bands were observed; therefore, tests were done to determine if the sequence obtained was expressed as functional RNA. RT-PCR from total RNA was performed with or without the initial reverse transcriptase step. Using two primers for the initial amplification, followed by a second round of PCR with an internal 'nested' primer, one band with the expected size of 300 bp was amplified. This band was dependent on the initial reverse transcriptase step indicating it was generated from RNA and not from low levels of contaminating genomic DNA. The sequence of this amplified product matched the sequence of the initial genomic DNA exactly, including in the region of the CCTAACCCT template.

Functional tests indicated that the cloned sequence represented the mouse telomerase RNA component. Investigations of co-purification with telomerase activity (Greider, C. W. and E. H. Blackburn (1987) supra) and for antisense oligonucleotide inhibition (Greider, C. W. and E. H. Blackburn (1989) supra) showed positive results. Telomerase was purified through chromatography over DEAE agarose, spermine agarose and phenyl sepharose; the telomerase activity was assayed, and RNA was prepared from all of the fractions. Northern analysis showed an RNA of approximately 550 bp was present in the active fractions of these columns. The RNA also co-purified with telomerase activity over a glycerol gradient. The size of the RNA in mouse cells is similar to that found in human cells. (Villeponteau, et al. (1995) in press).

Previous work with *Tetrahymena telomerase* showed that antisense oligonucleotides that cover the template inhibit telomerase and that oligonucleotides with 3' ends adjacent to the template are elongated by telomerase (Greider, C. W. and E. H. Blackburn (1989) supra; Lingner, et al. (1994) supra). oligonucleotides directed against the mouse RNA were examined for their effects on both inhibition and elongation of the mouse RNA. Oligonucleotides complementary to the candidate mouse telomerase RNA either covering the template region, MI-2, or hybridizing just 3' to the template MP-1, were tested for their ability to inhibit telomerase or serve as primers. For inhibition assays, each oligonucleotide was pre-incubated with mouse telomerase before the substrate d(TTAGGG)$_3$ was added. MI-2 which covers 11 nucleotides 3' of the template was an efficient inhibitor of telomerase activity at both 4 μM or 10 μM. Incubation with MP-1 or two other oligonucleotides that hybridize 3' of the template, MP-2 and MP-3, did not inhibit elongation, indicating that oligonucleotides that do not cross the template do not block elongation.

To determine the ability of the antisense oligonucleotides to serve as substrates, each oligonucleotide was added to a telomerase reaction in the absence of (TTAGGG)$_3$ primer. The oligonucleotide MP-1, whose 3' end is just adjacent to the 3' RNA template, was elongated by the addition of 8 residues and the addition of these products was RNase sensitive. Two control oligonucleotides, MP-2 and MP-3, were not elongated in this experiment. The addition of 8 nucleotides to MP-1 is consistent with the addition of the template complementary sequence AGGGTTAG onto the primer (see below).

To examine the specificity of the antisense primer inhibition and elongation, three control oligonucleotides (MI-3, MI-4 and MI-5) were synthesized. MI-4 extended RNA complementarity of MP-1 oligonucleotide through the template region of the RNA. This new oligonucleotide inhibited d(TTAGGG)$_3$ elongation so that it no longer served as a substrate for elongation although it has telomeric sequence at the 3' end.

To determine the specificity of MI-2 inhibition, the sequence of the 5' most 9 nucleotides of the oligonucleotide was changed so that it was no longer complementary to the RNA. This new oligonucleotide, MI-3, no longer inhibited d(TTAGGG)$_3$ elongation; however, it did serve as a substrate for elongation due to the 3' telomeric repeats. The predominant product migrated in the gel at position primer +5 as predicted since the 3' end of the oligonucleotide had the sequence TTAGG. Telomerase is expected to synthesize the five nucleotides GTTAG onto a primer with this 3' sequence.

As a last control, the 3' most 9 residues of the inhibitory MI-2 oligonucleotide were changed so that the resulting oligonucleotide (designated MI-5), would no longer hybridize to the CCUAACCCU template. MI-5 was not a telomerase substrate and did not inhibit d(TTAGGG)$_3$ elongation. Thus removing the complementarity of the antisense oligonucleotides abolished their ability to interact with telomerase in a predictable manner. To determine the inhibition efficiency of MI-2 and MI-4, telomerase was pre-incubated with a decreasing concentration of each antisense oligonucleotide prior to the addition of d(TTAGGG)$_3$, and then tested for elongation. Inhibition was complete at 0.2 μM for both oligonucleotides. These data show that the cloned RNA gene is a functional component of mouse telomerase.

Both mouse and Xenopus telomerase RNAs generate predominately one band during elongation. The position of the dissociation has been mapped to the first G residue in the sequence TTAG (Mantell, L. L. and C. W. Greider (1994) *EMBO J.* 13:1211–3217; Prowse, et al. (1993) supra). To determine the sequence added onto the MP-1 oligonucleotide, dideoxyTTP was substituted for the deoxyTTP in the elongation reaction. Telomerase reactions were carried out in the presence of $^{32}$P-dGTP, dATP and dTPP or $^{32}$P-dGTP, dATP and ddTPP. Using the primer (TTAGGG)$_3$ in the presence of dTTP, the typical predominant band at primer +4 was observed (Prowse, et al. (1993) supra). When ddTTP was substituted, all incorporation was abolished due to the incorporation of dTMP before the addition of labeled $^{32}$P-dGTP. Therefore, no labeled products are generated. Using MP-1, the 8 nucleotide labeled product observed with dTTP was reduced to 5 nucleotides in size when ddTTP was added. Again, this is consistent with the synthesis of AGGGTTAG onto the 3' end of the primer; chain termination with ddT inhibited the addition of the last TAG sequence.

If the entire potential template region of the mouse RNA, CCUAACCCU, were copied, and primer translocation occurred at the end of the template, a pause at the second G residue in the repeat d(TTAGGG) would be expected. Lingner, et al. (1994) supra; Greider, C. W. and E. H. Blackburn (1989) supra. Using permuted sequence primer oligonucleotides, both the human and the mouse telomerase enzymes pause or dissociate at the first G in the sequence. Prowse, et al. (1993) supra; Morin, G. B. (1989) supra. These data and the elongation of the antisense oligonucleotide describe above, show that the 5' most C which is present in the mouse but not the human template region does not serve as a template in the mouse RNA component. This is similar to the 5' most C in the *Stylonichia telomerase* RNA template which is apparently also not used as a template position (Lingner, et al. (1994) supra). Similarly, when an additional C residue was added to the 5' most border of the Tetrahymena template region, this extra C residue was not incorporated into reaction products (Autexier, C. and C. W. Greider (1994) unpublished data) indicating that there is an active mechanism to determine the boundaries of the template sequence within the telomerase RNA.

Primer extension and RT-PCR were used to characterize the 5' end of the mouse RNA. Northern analysis showed that the mouse and human telomerase RNAs are similar in size. Primer extension from total mouse RNA generated two distinct bands, one that mapped 20 nucleotides longer than the human 5' end and one that mapped 15 nucleotides shorter. To determine whether the RNA extends past the position of the mapped human 5' end, an oligonucleotide to this sequence was used in an RT-PCR reaction. Total RNA was reverse transcribed using random hexamers as primers. This cDNA was then amplified using an internal primer and an 18 nucleotide primer which would hybridize to the 5' most region identified by primer extension. A unique band of 450 nucleotides was generated and this product was further amplified with an internal nested primer, again the correct sized product of 200 nucleotides was generated. The products were cloned and the sequence corresponded to the genomic sequence shown in FIG. 4. This indicates that the RNA starts at the sequence 5' CUCGACC which is designated as +1 in the mouse sequence of FIG. 5. It is not yet determined whether the difference in start sites for the human and mouse telomerase RNAs is of functional significance. In FIG. 5, the conserved ribonucleotide residues between the human and mouse RNA sequences are boxed, and the template regions are boxed and highlighted in grey.

The expression of the RNA was assayed in cell lines and tissues where telomerase activity levels vary. Primary Mus spretus fibroblasts lack detectable telomerase activity and show telomere shortening similar to that found in human cells, while immortalized fibroblasts have telomerase activity. Northern analysis showed that immortalized fibroblasts expressed the 550 nucleotide RNA while it was not detected in primary cells with no telomerase activity. Similarly, the level of RNA present in mouse tissues paralleled the level of telomerase activity. RNA was detected in testes and liver both of which have high levels of telomerase activity. In addition, the RNA level was high in spleen. Telomerase activity is present in spleen although the relative level of activity compared to liver and testes is not known due to the presence of inhibitors in the crude spleen extracts.

As a general point regarding the nucleic acids and preparations containing the same of the invention, those of skill in the art recognize that the nucleic acids of the invention include both DNA and RNA molecules, as well as synthetic, non-naturally occurring analogues of the same, and heteropolymers of deoxyribonucleotides, ribonucleotides, and/or analogues of either. The particular composition of a nucleic acid or nucleic acid analogue of the invention will depend upon the purpose for which the material will be used and the environment(s) in which the material will be placed. Modified or synthetic, non-naturally occurring nucleotides, have been designed to serve a variety of purposes and to remain stable in a variety of environments, such as those in which nucleases are present, as is well known in the art. Modified or synthetic non-naturally occurring nucleotides, as compared to the naturally occurring nucleotides, as compared to the naturally occurring ribo- or deoxyribonucleotides, may differ with respect to the carbohydrate (sugar), phosphate linkage, or base portions, of the nucleotide, or may even contain a non-nucleotide base (or no base at all) in some cases. See, e.g., Arnold et al., PCT Patent Publication No. WO 89/02439, entitled "Non-nucleotide Linking Reagents for Nucleotide Probes" incorporated herein by reference.

Just as the nucleic acids of the invention can comprise a wide variety of nucleotides, so too can those nucleic acids serve a wide variety of useful functions. RNA probes or primers, especially those comprising a consecutive sequence of about 20 to 200 or more ribonucleotides encompassing conserved sequences between SEQ ID NO:1 and SEQ ID NO:3 are useful to detect telomerase RNA components in other species, and to inhibit or enhance telomerase activity as described below. DNA probes or primers encoding a consecutive sequence of about 20 to 200 or more ribonucleotides encompassing conserved sequences between SEQ ID NO:1 and SEQ ID NO:3, as well as DNA sequences that hybridize under moderately stringent conditions (Ausubel, et al. (1989) *Current Protocols in Molecular Biology*, John Wiley & Sons, N.Y.) to these conserved sequences may also be used for identification, diagnostic, assay and therapeutic purposes. In particular, both RNA and DNA probes may be used to identify telomerases and telomerase activity in other mammalian cells. RNA sequences that are substantially homologous to the conserved sequences between SEQ ID NO:1 and SEQ ID NO:3, or that hybridize to these conserved sequences under moderately stringent conditions are also within the scope of this invention.

Another especially useful type of nucleic acid of the invention is an antisense oligonucleotide that can be used in vivo or in vitro to inhibit the activity of human or another mammalian telomerase. Antisense oligonucleotides comprise a specific sequence of from about 10 to about 25 to 200 or more (i.e., large enough to form a stable duplex but small enough, depending on the mode of delivery, to administer in vivo, if desired) nucleotides complementary to a specific sequence of nucleotides in the RNA component of a mammalian telomerase. The mechanism of action of such oligonucleotides can involve binding of the RNA component either to prevent assembly of the functional ribonucleoprotein telomerase or to prevent the RNA component from serving as a template for telomeric DNA synthesis.

Illustrative antisense oligonucleotides of the invention that serve to inhibit telomerase activity in vivo and/or in vitro include the oligonucleotides mentioned above in connection with the tests to determine whether clone pGRN7 comprised the cDNA for the RNA component of human telomerase. Three such oligonucleotides were synthesized as 2'-O-methyl RNA olignucleotides and are more resistant to hydrolysis than unmodified RNA oligonucleotides, and, as noted above, were used to demonstrate inhibition of telomerase activity in vitro.

The sequence of each of these O-methyl RNA oligonucleotides is shown below.
T3 5'-CUCAGUUAGGGUUAGACAAA-3' (SEQ ID NO:6)
P3 5'-CGCCCUUCUCAGUUAGGGUUAG-3' (SEQ ID NO:7)
TA3 5'-GGCGCCUACGCCCUUCUCAGUU-3' (SEQ ID NO:8)

These oligonucleotides can also be used to inhibit telomerase activity in human cells.

Those of skill in the art will recognize that the present invention provides a wide variety of antisense oligonucleotides able to inhibit telomerase activity. Another useful antisense oligonucleotide of the invention is oligonucleotide Tel-AU, which has the sequence 5'-CAGGCCCACCCTCCGCAACC-3' (SEQ ID NO:9), and which, like any of the antisense oligonucleotides of the invention, can be synthesized using phosphorothioate nucleotides, chiral-methyl phosphonates, naturally occurring nucleotides, or mixtures of the same to impart stability and the desired $T_m$. Those of skill in the art recognize that a wide variety of modified nucleotide analogues, such as O-methyl ribonucleotides, phosphorothioate nucleotides, and methyl phosphonate nucleotides, can be used to produce nucleic acids of the invention with more desired properties (i.e., nuclease-resistant, tighter-binding, etc.) than those produced using naturally occurring nucleotides. Other techniques for rendering oligonucleotides nuclease-resistant include those described in PCT patent publication No. 94/12633.

In addition, to the antisense oligonucleotides of the invention, one can construct oligonucleotides that will bind to duplex nucleic acid either in the folded RNA component or in the gene for the RNA component, forming a triple helix-containing or triplex nucleic acid to inhibit telomerase activity. Such oligonucleotides of the invention are constructed using the base-pairing rules of triple helix formation and the nucleotide sequence of the RNA component. Such oligonucleotides can block telomerase activity in a number of ways, including by preventing transcription of the telomerase gene or by binding to a duplex region of the RNA component of telomerase in a manner that prevents the RNA component either from forming a functional ribonucleoprotein telomerase or from serving as a template for telomeric DNA synthesis. Typically, and depending on mode of action, the triplex-forming oligonucleotides of the invention comprise a specific sequence of from about 10 to about 25 to 200 or more (i.e., large enough to form a stable triple helix but small enough, depending on the mode of delivery, to administer in vivo, if desired) nucleotides "complementary" (in this context, complementary means able to form a stable triple helix) to a specific sequence in the RNA component of telomerase or the gene for the RNA component of telomerase.

In addition to the antisense and triple helix-forming oligonucleotides of the invention, "sense" oligonucleotides identical in sequence to at least a portion of the RNA component of human telomerase or another mammalian telomerase can also be used to inhibit telomerase activity. Oligonucleotides of the invention of this type are characterized in comprising either (1) less than the complete sequence of the RNA component needed to form a functional telomerase enzyme or (2) the complete sequence of the RNA component needed to form a functional telomerase enzyme as well as a substitution or insertion of one or more nucleotides that render the resulting RNA non-functional. In both cases, inhibition of telomerase activity is observed due to the "mutant" RNA component binding the protein components of the telomerase to form an inactive telomerase molecule. The mechanism of action of such oligonucleotides thus involves the assembly of a non-functional ribonucleoprotein telomerase or the prevention of assembly of a functional ribonucleoprotein telomerase. Sense oligonucleotides of the invention of this type typically comprise a specific sequence of from about 20, 50, 200, 400, 500, or more nucleotides identical to a specific sequence of nucleotides in the RNA component of a telomerase.

Thus, another oligonucleotide of the invention comprises an altered or mutated sequence of the RNA component of human or another mammalian telomerase. Yu, et al. (1990) Nature 344:126, shows that a mutated form of the RNA component of Tetrahymena telomerase can be incorporated into the telomerase of Tetrahymena cells and that the incorporation has deleterious effects on those cells. Incorporation of mutated forms of the RNA component of human or another mammalian telomerase may have similar effects on human or mammalian cells that otherwise have telomerase activity without affecting normal human cells that do not have telomerase activity. Such mutated forms include those in which the sequence 5'-CTAACCCTA-3' is mutated to 5'-CAAACCCAA-3', 5'-CCAACCCCAA-3', or 5'-CTCACCCTCA-3'. Each of these altered RNA component sequences alters the telomeric repeat units incorporated into the chromosomal DNA, thus affecting chromosome structure and function. Such oligonucleotides can be designed to contain restriction enzyme recognition sites useful in diagnostic methods for the presence of the altered RNA component via restriction enzyme digestion of telomeric DNA or an extended telomerase substrate.

To illustrate this aspect of the invention, site-specific mutagenesis was carried out using a plasmid (designated pGRN33, available from the American Type Culture Collection under ATCC accession No. 75926) that comprises an ~2.5 kb HindIII-SacI fragment from lambda clone 28-1 (see Example 7, below) as well as the SV40 origin of replication (but no promoter activity). The resulting plasmids, designated pGRN34 (comprising 5'-CAACCCAA-3'), pGRN36 (comprising 5'-CCAACCCCAA-3'), and pGRN37 (comprising 5'-CTCACCCTCA-3'), were transformed into eukaryotic host cells (a 293-derived cell line expressing SV40 large T antigen), and telomerase assays were conducted using cell extracts from the transformants.

The assays showed that the telomerase activity in the cells resulted in the formation of nucleic acids comprising the altered sequences, indicating that the genomic clone comprised a functional RNA component gene and that the plasmids comprised an altered but functional RNA component gene. These results illustrate how the present invention provides recombinant telomerase preparations and methods for producing such preparations. The present invention provides a recombinant human or mammalian telomerase in functional association with a recombinant RNA component of the invention. Such recombinant RNA component molecules of the invention include those that differ from naturally occurring RNA component molecules by one or more base substitutions, deletions, or insertions, as well as RNA component molecules identical to a naturally occurring RNA component molecule that are produced in recombinant host cells. The method for producing such recombinant telomerase molecules comprises transforming a eukaryotic host cell that expresses the protein components of telomerase with a recombinant expression vector under conditions such that the protein components and RNA components are expressed and assemble to form an active telomerase molecule capable of adding sequences (not necessarily the same sequence added by native telomerase) to telomeres of chromosomal DNA. Other useful embodiments of such recombinant DNA expression vectors (or plasmids) include plasmids that comprise the gene for the RNA component of human telomerase with a deletion, insertion, or other modification that renders the gene non-functional. Such plasmids are especially useful for gene therapy to "knock-out" the endogenous RNA component gene, although a highly efficient transformation and recombination system is required, to render the treated cells irreversibly mortal.

Other oligonucleotides of the invention called "ribozymes" can also be used to inhibit telomerase activity. Unlike the antisense and other oligonucleotides described above, which bind to an RNA, a DNA, or a telomerase protein component, a ribozyme not only binds but also specifically cleaves and thereby potentially inactivates a target RNA, such as the RNA component of human telomerase. Such a ribozyme can comprise 5'- and 3'-terminal sequences complementary to the telomerase RNA. Depending on the site of cleavage, a ribozyme can render the telomerase enzyme inactive. See PCT patent publication No. 93/23572, supra. Those in the art upon review of the RNA sequence of the human or mouse telomerase RNA component will note that several useful ribozyme target sites are present and susceptible to cleavage by, for example, a hammerhead motif ribozyme. Illustrative human ribozymes of the invention of this type include the ribozymes below, which are RNA molecules having the sequences indicated:

```
1: 5'-UAGGGUUACUGAUGAGUCCGUGAGGACGAAACAAAAAAU-3'    (SEQ ID NO:10)

2: 5'-UUAGGGUCUGAUGAGUCCGUGAGGACGAAAGACAAAA-3'     (SEQ ID NO:11)

3: 5'-UCUCAGUCUGAUGAGUCCGUGAGGACGAAAGGGUUA-3'      (SEQ ID NO:12)

4: 5'-CCCGAGACUGAUGAGUCCGUGAGGACGAAACCCGCG-3'      (SEQ ID NO:13).
```

Other optimum target sites for ribozyme-mediated inhibition of telomerase activity can be determined as described by Sullivan, et al., PCT patent publication No. 94/02595 and Draper, et al., PCT publication No. 93/23569, both incorporated herein by reference. As described by Hu, et al., PCT patent publication No. 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

Thus, the invention provides a wide variety of oligonucleotides to inhibit telomerase activity. Such oligonucleotides can be used in the therapeutic methods of the invention for treating disease, which methods comprise administering to a patient a therapeutically effective dose of a telomerase inhibitor or activator of the invention. One can measure telomerase inhibition or activation to determine the amount of an agent that should be delivered in a therapeutically effective dose using the assay protocols described in the copending U.S. patent applications and PCT patent publication No. 93/23572 noted above. As noted in those application and discussed above, inhibition of telomerase activity renders an immortal cell mortal, while activation of telomerase activity can increase the replicative lifespan of a cell. Telomerase inhibition therapy is an effective treatment against cancers involving the uncontrolled growth of immortal cells, and telomerase activation is an effective treatment to prevent cell senescence. Delivery of agents that inhibit or block telomerase activity, such as an antisense oligonucleotide, a triple helix-forming oligonucleotide, a ribozyme, or a plasmid that drives expression of a mutant RNA component of telomerase can prevent telomerase action and ultimately leads to cell senescence and cell death of treated cells.

In addition, the present invention provides therapeutic methods that ensure that normal cells remain mortal; for instance, the RNA component can be modified using standard genetic engineering procedures to delete all or a portion of a natural gene encoding the component (e.g., by in vitro mutagenesis) by genetic recombination. Such cells will then be irreversibly mortal. This procedure is useful in gene therapy, where normal cells modified to contain expression plasmids are introduced into a patient, and one wants to ensure cancerous cells are not introduced or, if such cells are introduced, then those cells have been rendered irreversibly mortal.

Because telomerase is active only in tumor, germline, and certain stem cells of the hematopoietic system in humans, other normal cells are not affected by telomerase inhibition therapy. Steps can also be taken to avoid contact of the telomerase inhibitor with germline or stem cells, although this may not be essential. For instance, because germline cells express telomerase activity, inhibition of telomerase may negatively impact spermatogenesis and sperm viability, suggesting that telomerase inhibitors may be effective contraceptives or sterilization agents. This contraceptive effect may not be desired, however by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient.

Other therapeutic methods of the invention employ the telomerase RNA nucleic acid of the invention to stimulate telomerase activity and to extend replicative cell life span. These methods can be carried out by delivering to a cell a functional recombinant telomerase ribonucleoprotein of the invention to the cell. For instance, the ribonucleoprotein can be delivered to a cell in a liposome, or the gene for the RNA component of human telomerase (or a recombinant gene with different regulatory elements) can be used in a eukaryotic expression plasmid (with or without sequences coding for the expression of the protein components of telomerase) to activate telomerase activity in various normal human cells that otherwise lack detectable telomerase activity due to low levels of expression of the RNA component or a protein component of telomerase. If the telomerase RNA component is not sufficient to stimulate telomerase activity, then the RNA component can be transfected along with genes expressing the protein components of telomerase to stimulate telomerase activity. Thus, the invention provides methods for treating a condition associated with the telomerase activity within a cell or group of cells by contacting the cell(s) with a therapeutically effective amount of an agent that alters telomerase activity in that cell.

Cells that incorporate extra copies of the telomerase RNA gene can exhibit an increase in telomerase activity and an associated extended replicative life span. Such therapy can be carried out ex vivo on cells for subsequent introduction into a host or can be carried out in vivo. The advantages of stabilizing or increasing telomere length by adding exogenous telomerase genes ex vivo to normal diploid cells include: telomere stabilization can arrest cellular senescence and allow potentially unlimited amplification of the cells; and normal diploid cells with an extended life span can be cultured in vitro for drug testing, virus manufacture, or other useful purposes. Moreover, ex vivo amplified stem cells of various types can be used in cell therapy for particular diseases, as noted above.

Telomere stabilization can also suppress cancer incidence in replicating cells by preventing telomeres from becoming critically short as cells near crisis. During crisis, massive genomic instability is generated as the protective effect of the telomeric cap is lost. The "genetic deck" is reshuffled, and almost all cells die. The rare cells that emerge from this process are typically aneuploid with many gene rearrangements and end up reestablishing stability in their telomeres by expressing telomerase. If crisis can be prevented by keeping telomeres long, then the genomic instability associated with crisis can also be prevented, limiting the chances than an individual cell will suffer the required number of genetic mutations needed to spawn a metastatic cancer.

Cells that can be targeted for telomerase gene therapy (therapy involving increasing the telomerase activity of a target cell) in humans include but are not limited to hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

Typically, the therapeutic methods of the invention involve the administration of an oligonucleotide or drug that functions to inhibit or stimulate telomerase activity under in vivo physiological conditions and will be stable under those conditions. As noted above, modified nucleic acids may be useful in imparting such stability, as well as for ensuring delivery of the oligonucleotide to the desired tissue, organ, or cell. Methods useful for delivery of oligonucleotides for therapeutic purposes are described in Inouye et al., U.S. Pat. No. 5,272,065, incorporated herein by reference.

While oligonucleotides can be delivered directly as a drug in a suitable pharmaceutical formulation, one can also deliver oligonucleotides using gene therapy and recombinant DNA expression plasmids of the invention. One such illustrative plasmid is described in Example 8, below. In general, such plasmids will comprise a promoter and, optionally, an enhancer (separate from any contained within the promoter sequences) that serve to drive transcription of an oligoribonucleotide, as well as other regulatory elements that provide for episomal maintenance or chromosomal integration and for high-level transcription, if desired. Adenovirus-based vectors are often used for gene therapy and are suitable for use in conjunction with the reagents and methods of the present invention. See PCT patent publication Nos. 94/12650; 94/12649; and 94/12629. Useful promoters for such purposes include the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), and the constitutive CMV promoter. A plasmid useful for gene therapy can comprise other functional elements, such as selectable markers, identification regions, and other genes. Recombinant DNA expression plasmids can also be used to prepare the oligonucleotides of the invention for delivery by means other than by gene therapy, although it may be more economical to make short oligonucleotides by in vitro chemical synthesis.

In related aspects, the invention features pharmaceutical compositions including a therapeutically effective amount of a telomerase inhibitor or telomerase activator of the invention. Pharmaceutical compositions of telomerase inhibitors of the invention include a mutant RNA component of human or another mammalian telomerase, an antisense oligonucleotide or triple helix-forming oligonucleotide that binds the RNA component or the gene for the same of human or another mammalian telomerase, or a ribozyme able to cleave the RNA component of human or another mammalian telomerase, or combinations of the same or other pharmaceuticals in a pharmaceutically acceptable carrier or salt. Other pharmaceutical compositions of the invention comprise a telomerase activator preparation, such as purified human telomerase or mRNA for the protein components of telomerase and the RNA component of telomerase, and are used to treat senescence-related disease. The therapeutic agent can be provided in a formulation suitable for parenteral, nasal, oral, or other mode of administration. See PCT patent publication No. 93/23572, supra.

The present invention provides diagnostic methods and reagents in addition to the pharmaceutical formulations and therapeutic methods described above. The invention provides diagnostic methods for determining the level, amount, or presence of the RNA component of telomerase, telomerase, or telomerase activity in a cell, cell population, or tissue sample. In a related aspect, the present invention provides useful reagents for such methods, optionally packaged into kit form together with instruction for using the kit to practice the diagnostic methods.

In addition, probes or primers that bind specifically to the RNA component of a telomerase (or either strand of the gene for the same) can be used in diagnostic methods to detect the presence of telomerase nucleic acid in a sample. Primers and probes are oligonucleotides that are complementary, and so will bind, to a target nucleic acid. Although primers and probes can differ in sequence and length, the primary differentiating factor is one of function: primers serve to initiate DNA synthesis, as in PCR amplification, while probes are typically used only to bind to a target nucleic acid. Typical lengths for a primer or probe can range from 8 to 20 to 30 or more nucleotides. A primer or probe can also be labeled to facilitate detection (i.e., radioactive or fluorescent molecules are typically used for this purpose) or purification/separation (i.e., biotin or avidin is often used for this purpose).

An especially preferred diagnostic method of the invention involves the detection of telomerase RNA component sequences in cell or tissue samples taken from patients suspected to be at risk for cancer. Such methods will typically involve binding a labelled probe or primer to an RNA component sequence under conditions such that only perfectly matched (complementary) sequences bind (hybridize) to one another. Detection of labelled material bound to RNA in the sample can correlate with the presence of telomerase activity and the presence of cancer cells. The diagnostic methods of the invention may be especially useful in detecting the presence of telomerase activity in tissue biopsies and histological sections in which the method is carried out in situ, typically after amplification of telomerase RNA component using specific PCR primers of the invention.

Depending on the length and intended function of the primer, probe, or other nucleic acid comprising sequences from the RNA component of a telomerase, expression plasmids of the invention may be useful. For instance, recombinant production of the full-length RNA component of human telomerase can be carried out using a recombinant DNA expression plasmid of the invention that comprises a nucleic acid comprising the nucleotide sequence of the RNA component positioned for transcription under the control of a suitable promoter. Host cells for such plasmids can be either prokaryotic or eukaryotic, and the promoter, as well as the other regulatory elements and selectable markers chosen for incorporation into the expression plasmid will depend upon the host cell used for production.

The intact RNA components gene, i.e., the promoter, which includes any regulatory sequences in the 5'-region of the gene, and RNA component coding region, can be used to express the RNA component in human cells, including human cells that have been immortalized by viral transformation or cancer. The promoter of the RNA component gene may be regulated, however, and for this and other reasons, one may want to express the RNA component under the control of a different promoter. On the other hand, the promoter of the RNA component gene can be used independently of the RNA component coding sequence to express other coding sequences of interest. For instance, one could study the transcriptional regulation of the RNA component gene by fusing the promoter of the RNA component gene to a coding sequence for a "reporter" coding sequence, such as the coding sequence for beta-galactosidase or another enzyme or protein the expression of which can be readily monitored. Thus, the promoter and other regulatory elements of the gene for the RNA component of human telomerase can be used not only to express the RNA component but also protein components of human telomerase, antisense or other oligonucleotides, as well as other gene products of interest in human cells. Expression plasmids comprising the intact gene for the RNA component of human telomerase can be especially useful for a variety of purposes, including gene therapy. Those of skill in the art recognize that a wide variety of expression plasmids can be used to produce useful nucleic acids of the invention and that the term "plasmid", as used herein, refers to any type of nucleic acid (from a phage, virus, chromosome, etc.) that can be used to carry specific genetic information into a host cell and maintain that information for a period of time.

As indicated by the foregoing description, access to purified nucleic acids comprising the sequence of the RNA component of a telomerase provides valuable diagnostic and therapeutic methods and reagents, as well as other important benefits. One important benefit of the present invention is that the methods and reagents of the invention can be used to isolate the RNA component and genes for the RNA component of telomerase from any other mammalian species that has an RNA component substantially homologous to the human, mouse, or rat coding region of the RNA component of the present invention. The phrase "substantially homologous" refers to that degree of homology required for specific hybridization of an oligonucleotide or nucleic acid sequence of the human, mouse or rat RNA component to a nucleic acid sequence of an RNA component sequence of another mammalian species. Given such substantial homology, those of ordinary skill in the art can use the nucleic acids and oligonucleotide primers and probes of the invention to identify and isolate substantially homologous sequences.

For instance, one can probe a genomic or cDNA library to detect homologous sequences. One can also use primers corresponding to regions of the RNA component sequence and PCR amplification under low or moderate stringency conditions to amplify a specific homologous nucleic acid sequence from preparations of RNA or DNA from a mammalian species. By using these and other similar techniques, those of ordinary skill can readily isolate not only variant RNA component nucleic acid from human or mouse cells but also homologous RNA component nucleic acids from other mammalian cells, such as cells from primates, from mammals of veterinary interest, i.e., cattle, sheep, horses, dogs, and cats, and from other rodents, i.e., hamsters. An example of this application, wherein mouse RNA component is isolated and sequenced, has already been described. Example 15 also illustrates how such methodology has been used to identify and isolate the partial sequence of the rat RNA component and RNA component sequences of primates. Further, probes or primers that comprise nucleotide sequences encoding conserved ribonucleotides between the mouse and human telomerase RNA components are especially useful for this purpose because they are most likely to be conserved and constitute part of the RNA component in other mammals.

The reagents of the present invention also allow the cloning and isolation of nucleic acids encoding the protein components of human as well as other mammalian telomerase enzymes, which have not previously been available. Access to such nucleic acids provide complementary benefits to those provided by the nucleic acids comprising nucleic acid sequences of the RNA component of human or other mammalian telomerases. For instance, and as noted above, the therapeutic benefits of the present invention can be enhanced, in some instances, by use of purified preparations of the protein components of human telomerase and by access to nucleic acids encoding the same. The nucleic acids of the invention that encode the RNA component of human telomerase can be used to isolate the nucleic acid encoding the protein components of human telomerase, allowing access to such benefits. Thus, the invention provides methods for isolating and purifying the protein components of human telomerase, as well as for identifying and isolating nucleic acids encoding the protein components of human telomerase. In related aspects, the present invention provides purified human telomerase, purified nucleic acids that encode the protein components of human telomerase, and recombinant expression plasmids for the protein components of human telomerase. The invention also provides pharmaceutical compositions comprising as an active ingredient either the protein components of human telomerase or a nucleic acid that either encodes those protein components or interacts with nucleic acids that encode those protein components, such as antisense oligonucleotides, triple helix-forming oligonucleotides, ribozymes, or recombinant DNA expression plasmids for any of the foregoing.

The cloned RNA component of human, mouse, or rat telomerase can be used to identify and clone nucleic acids encoding the protein components of the ribonucleoprotein telomerase enzyme. Several different methods can be employed to achieve identification and cloning of the protein components. For instance, one can use affinity capture of the enzyme or partially denatured enzyme using as a affinity ligand either (1) nucleotide sequences complementary to the RNA component to bind to the RNA component of the intact enzyme; or (2) the RNA component to bind the protein components of a partially or fully denatured enzyme. The ligand can be affixed to a solid support or chemically modified (e.g., biotinylated) for subsequent immobilization on the support. Exposure of cell extracts containing human telomerase, followed by washing and elution of the telomerase enzyme bound to the support, provides a highly purified preparation of the telomerase enzyme. The protein components can then be optionally purified further or directly analyzed by protein sequencing. The protein sequence determined can be used to prepare primers and probes for cloning the cDNA or identifying a clone in a genomic bank comprising nucleic acids that encode a protein component of telomerase.

Affinity capture of telomerase utilizing an engineered RNA component can also be conducted using in vitro transcribed telomerase RNA and a system for the reconstitution of telomerase enzyme activity. See Autexier, C. and C. W. Greider (1994) *Genes & Development* 8:563–575, incorporated herein by reference. The RNA is engineered to contain a tag, similar to epitope tagging of proteins. The tag can be an RNA sequence to which a tightly binding ligand is available, e.g., an RNA sequence-specific antibody, a sequence-specific nucleic acid binding protein, or an organic dye that binds tightly to a specific RNA sequence. The tolerance of telomerase for the tag sequence and position can be tested using standard methods. Synthesis of the altered RNA component and the reconstitution step of this method can also be carried on in vivo. Affinity capture using the immobilized ligand for the RNA tag can then be used to isolate the enzyme.

Expression screening can also be used to isolate the protein components of the telomerase enzyme. In this method, cDNA expression libraries can be screened with labeled telomerase RNA, and cDNAs encoding proteins that bind specifically to telomerase RNA can be identified. A molecular genetic approach using translational inhibition can also be used to isolate nucleic acids encoding the protein components of the telomerase enzyme. In this method, telomerase RNA sequences will be fused upstream of a selectable marker. When expressed in a suitable system, the selectable marker will be functional. When cDNA encoding a telomerase RNA binding protein is expressed, the protein will bind to its recognition sequence thereby blocking translation of the selectable marker, thus allowing for identification of the clone encoding the protein. In other embodiments of this method, the blocked translation of the selectable marker will allow transformed cells to grow. Other systems that can be employed include the "interaction trap system" described in PCT patent publication No. WO 94/10300; the "one-hybrid" system described in Li and Herskowitz (1993) *Science* 262:1870–1874, and Zervos, et al. (1993) *Cell* 72:223–232; and the "two-hybrid" system commercially available from Clontech.

Telomerase RNA binding or telomerase activity assays for detection of specific binding proteins and activity can be used to facilitate the purification of the telomerase enzyme and the identification of nucleic acids that encode the protein components of the enzyme. For example, nucleic acids comprising RNA component sequences can be used as affinity reagents to isolate, identify, and purify peptides, proteins or other compounds that bind specifically to a sequence contained within the RNA component, such as the protein component of human telomerase. Several different formats are available, including gel shift, filter binding, footprinting, Northwestern (RNA probe of protein blot), and photocrosslinking, to detect such binding and isolate the components that bind specifically to the RNA component. These assays can be used to identify binding proteins, to track purification of binding proteins, to characterize the RNA binding sites, to determine the molecular size of binding proteins, to label proteins for preparative isolation, and for subsequent immunization of animals for antibody generation to obtain antibodies for use in isolating the protein or identifying a nucleic acid encoding the protein in a coupled transcription/translation system.

The mouse or rat RNA components have many additional uses. Like the human RNA component, they can be used to prepare transgenic animals of great value for screening and testing of pharmaceuticals that regulate telomerase activity.

For instance, by using a plasmid, one can "knock out" the RNA component gene or replace the natural RNA component gene with a recombinant inducible gene in a *Mus muculus* embryonic stem cell and then generate a transgenic mouse that will be useful as a model or test system for the study of cancer, or age- or senescence-related disease. The generation of mice and mouse cells lacking telomerase makes it possible to determine the effects of telomerase inhibitors directly. In addition, the toxicity of telomerase inhibitors can be assessed in an animal model where the specific target has been removed. Thus, any side effects of such inhibitors will be revealed in the mouse model.

Initially a knockout mouse is generated with one of the two telomerase alleles deleted. As an example of a knockout plasmid that could be used for this task, a plasmid vector has been constructed (FIG. 6) using standard cloning procedures. Sambrook, et al. (1989) supra. In this plasmid, the entire telomerase RNA gene has been eliminated and replaced by the bacterial neomycin gene (neo). The restriction map of the mouse telomerase RNA genomic region is shown in FIG. 6, as well as the sections that were cloned into the knockout vector. This plasmid can be used to generate knockout mice from a number of *Mus musculus* ES cell strains.

Mouse model systems can also be used to study telomerase regulation and telomere length in mammals. Similar to human cells, mouse fibroblasts show no telomerase activity during growth while telomere length decreases until the culture passes through crisis when telomerase activity is detected as the telomere length stabilizes. Furthermore, telomere lengths from tissues of individual adult mice differ between tissues. For example, testes telomere length is significantly longer than in other tissues, suggesting that a developmentally-regulated telomere length increase may occur after birth. Thus the mouse offers an excellent system in which to directly test the role of telomerase in aging and immortalization because the effects of altered telomerase on both cell viability and organismal development can be determined in vivo.

The same or another mammalian system can be used to test the effects of therapeutic and pharmaceutical compounds on telomerase activity. Anti-telomerase compositions, including antibodies, directed towards telomerase activity in tumors can be screened for efficacies and side effects.

As will be apparent to those of skill in the art upon reading of this disclosure, the present invention provides valuable reagents relating to human or mammalian telomerases, as well as a variety of useful therapeutic and diagnostic methods, and model systems. The above description of necessity provides a limited sample of such methods, which should not be construed as limiting the scope of the invention. Other features and advantages of the invention will be apparent from the following examples and claims.

The following examples describe specific aspects of the invention to illustrate the invention and provide a description of the methods used to isolate and identify the RNA component of both human telomerase and mouse telomerase, and the partial sequence of rat telomerase, for those of skill in the art. The examples should not be construed as limiting the invention, as the examples merely provide specific methodology useful in understanding and practice of the invention.

EXAMPLE 1

Preparation of PCT-amplifiable cDNA

RNA was obtained from 293 cells by guanidine-thiocyanate extraction of from purified telomerase fractions by phenol/chloroform extractions. The total RNA from 293 cells was size fractionated on a 2% agarose gel, and the RNA below 500 bp was isolated.

First strand cDNA synthesis was performed with Superscript™ II reverse transcriptase obtained from Bethesda Research Laboratories (BRL). About 0.5 to 1.0 μg RNA was mixed with about 40 ng of random primer (6 mer) in water at a total volume of 11 μl. The solution was heated for 10 min. at 95° C. and then cooled on ice for 5–10 min. The denatured nucleic acid was collected by centrifugation. The denatured RNA and primer mixture were then resuspended by adding, in the order shown: 4 μl 5x 1st strand synthesis buffer; 2 μl 0.1 M dithiothreitol (DTT); 1 μl RNAsin (Pharmacia); and 1 μl dNTP (0.125 mM each for 0.5 mM total concentration). The reaction mixture was incubated at 42° C. for 1 min., and then, 1 µl (200 units) of Superscript™ II RTase (BRL) was added and mixed into the reaction, which was then incubated for 60 min. at 42° C. The resulting reaction mixture, containing the newly synthesized cDNA was placed on ice until second strand synthesis was performed.

Second strand cDNA synthesis was performed as follows: About 20 µl of the reaction mixture from the first strand cDNA synthesis reaction mixture (from above) was mixed with, in the order shown, the following components: 111.1 µl of water; 16 µl of 10x E. coli DNA ligase buffer; 3 µl of dNTP (2.5 mM each stock); 1.5 µl of E. coli DNA ligase (15 units from BRL); 7.7 µl of E. coli DNA polymerase (40 units from Pharmacia); and 0.7 µl of E. coli RNase H (BRL). The resulting solution was gently mixed and incubated for 2 hours at 16° C., at which time 1 µl (10 units) of T4 DNA polymerase was added to the reaction tube and incubation continued for 5 min. at the same temperature (16° C.) . The reaction was stopped, and the nucleic acid was collected by extracting the reaction with phenol/chloroform twice, precipitating the nucleic acid with ethanol, and centrifuging the reaction mixture to pellet the nucleic acid.

The cDNA pellet collected by centrifugation was resuspended in 20 µl of TE buffer and ligated to a double-stranded oligonucleotide called "NotAB" composed of two oligonucleotides (NH2 is an amino blocking group):
NotA: 5'-pATAGCGGCCGCAAGAATTCA-NH2 (SEQ ID NO:14)
NotB: 5'-TGAATTCTTGCGGCCGCTAT-3' (SEQ ID NO:15)
The double-stranded oligonucleotide was made by mixing 50 µ of NotA oligonucleotide (100 pmol) with 50 µl of NotB oligonucleotide (100 pmol) in 46.25 µl of water, heating the resulting solution for 5 min. at 95° C., and adding 3.75 µl of 20x SSC buffer while the solution was still hot. The tube containing the mixture was then placed in a beaker containing hot water (at a temperature of about 70 to 75° C.), the temperature of which was allowed to drop slowly to below 15° C., so that the two oligonucleotides could hybridize to form the double-stranded oligonucleotide NotAB. The resulting nucleic acid was collected by precipitation and centrifugation.

The double-stranded NotAB oligonucleotide was resuspended in about 30 µl TE buffer and then ligated to the cDNA in a reaction mixture containing 10 µl of the cDNA preparation described above, about 50 pmol (calculated by OD260) of NotAB; 2 µl of 10x T4 DNA ligase buffer; 1.2 µl of T4 DNA ligase; 0.2 µl of 10 mM ATP; and water in a total volume of 20 µl by incubating the reaction mixture at 16° C. overnight. The reaction was then heat-inactivated by heating the reaction mixture for 10 min. at 65° C. About 1 to 2 µl of the resulting mixture was typically used for PCR amplification; one can amplify the ligation mixture for 10 to 15 cycles (94° C., 45 seconds; 60° C., 45 seconds; and 72° C., 1.5 min.) and save as a stock, as described in Example 2.

EXAMPLE 2

PCR Amplification of cDNA

The cDNA was routinely amplified by preparing an amplification reaction mixture composed of 5 µl of 10x PCR buffer (500 mM KCL; 100 mM Tris, ph=8.3; and 20 mM MgCl$_2$; 5–8 µl of dNTP (2.5 mM each); 1 µl of Taq polymerase (Boehringer-Mannheim); 0.1 µl of gene 32 protein (Boehringer-Mannheim); 6 µl of Not B primer (20 µM stock); 2 µl of the cDNA (prepared as described in Example 1), and water to 50 µl. This mixture was then overlaid with 50 to 100 µl of mineral oil, and PCR amplification was performed for 10 to 15 cycles of 94° C., 45 seconds; 60° C., 45 seconds; and 72° C., 1.5 min. After amplification, the reaction mixture was extracted with phenol/chloroform, and the amplified nucleic acid was precipitated with ethanol and collected by centrifugation. The precipitate was then dissolved in 100 µl of TE buffer to prepare a stock solution.

EXAMPLE 3

PCR Amplification for Cyclic Selection

To make PCR product for cyclic selection, about 1 µl of a stock solution prepared as described in Example 2 was amplified in 50 µl of PCR reaction mixture prepared as described in Example 2, except that 21–24 cycles of primer annealing, extension, and denaturation of product were conducted. After amplification, reaction mixtures were extracted with phenol/chloroform, precipitated with ethanol, and collected by centrifugation. Product yield was estimated by staining with ethidium bromide after agarose gel electrophoresis of a small aliquot of the reaction mixture. Typically, about 2 µg of the nucleic acid product were used for cyclic selection.

After cyclic selection, described in Example 4, about 1 to 2 µl of the selected "pull-down" products (out of a total volume of 20 µl) were PCR amplified as described in Example 2 for 22 cycles, precipitated with ethanol, and collected by centrifugation in preparation for further cyclic selection.

EXAMPLE 4

Positive Selection of PCT-amplified cDNA

For the positive selection step of the cyclic selection process used to clone the RNA component of human telomorase, about 2 µg of the PCR-amplified cDNA were diluted into 25 µl of TE buffer and then mixed with 1.25 µl of 20X SSC and the resulting solution heated to 95° C. for 3 min. The temperature was lowered to 60° C. for 5 min., and one µl (0.1 µg/µl) of the R2 or R4 biotinylated probe was added. The sequences of these probes are shown below. The probes are O-methyl-RNA probes, so U is O-methyl-uridine, A is O-methyl-riboadenine, G is O-methyl-riboguanine, and I is inosine.
R2: 5'-UUAGGGUUAGII-biotin
R4: 5'-AUUGGGUUAUII-biotin
The R2 probe is specific for the telomere repeat, and the R4 probe is specific for RNase P, which was used to track the effectiveness and efficiency of the cyclic selection process. By carrying out a cyclic selection simultaneously but separately for RNase P RNA, a molecule of known sequence, one can have greater confidence that the cyclic selection process is functioning properly with respect to the molecule of interest, in this case the RNA component of human telomerase.

After either the R2 or R4 probe was added to the mixture at 65° C., the temperature of the hybridization reaction mixture was lowered to 30° C. by incubating the mixture at that temperature for 5 min., and then the reaction mixtures were further lowered to a temperature of 14° C. by incubating at that temperature for 60 min. Finally, the mixture was incubated at 4° C. for 2–12 hours.

The entire hybridization reaction mixture for each sample (R2 or R4) was added to 400 µl of 0.5X SSC at 4° C. and then added to a tube of ice-cold magnetic beads, which were purchased from Promega and pre-washed four times with 0.5X SSC before use. The resulting mixture was incubated 30 min. at 4° C. to ensure complete binding to the magnetic beads. Each reaction tube was then incubated briefly at room temperature on the magnetic stand (Promega) to pull down the beads. The beads were resuspended in cold 0.5X SSC (600 μl) and placed (in a tube) on ice. The samples were washed three more times with 0.5X SSC in this manner. Nucleic acid was eluted from the beads by resuspending the beads in 100 μl of water and incubating for 2 min. at 65° C. before placing-the beads back on the magnetic stand for collection. This process was repeated three more times; the last time, the resuspended beads were incubated for 5 min. at 65° C. before placing the beads on the magnetic stand for collection. All of the 100 μl supernatants (for each sample) were pooled and dried down to 20 μl in a SpeedVac™ centrifuge. The recovered DNA was then PCR amplified for another round of amplification and selection. After each amplification, the PCR products were phenol-chloroform extracted twice, ethanol precipitated, and resuspended in 20 μl of TE buffer.

Typically, PCR amplifications were verified by agarose gel electrophoresis. In addition, a variety of controls were used to monitor the cyclic selection process. As one control, PCR "arms" (oligonucleotides of defined sequence that serve as primer hybridization sites) were placed on a nucleic acid that comprised a neomycin resistance-conferring gene. The resulting nucleic acid was mixed with the PCR-amplified cDNA and monitored at each selection by quantitative PCR. As another control, RNase P was followed in both the RNase P selected and the telomerase RNA component selected libraries.

EXAMPLE 5

RT-PCR Protocol

The first strand cDNA was made in substantial accordance with the procedure described in Example 1. Basically, RNA was purified from each telomerase fraction containing 0.1 to 1 μg RNA; typical, about one-third to one-fifth of the RNA made from a 300 μl fraction was used. The RNA was mixed with 40 to 80 ng random hexamer in 10 μl, denatured for 10 min. at 95° C. (using a thermal-cycling instrument), and chilled on ice. The denatured RNA and 6-mer were added to a reaction mixture containing 4 μl of 5x 1st strand synthesis buffer supplied by the manufacturer of the reverse transcriptase (RTase, purchased from BRL), 2 μl of 0.1 DTT, 1 μl of 10 mM dNTP (each), 1 μl of RNase inhibitor (Pharmacia), and water to a total volume of 9 μl. The combined mixture was placed into a 42° C. water bath. After 1–2 min. incubation, 1 μl of Superscript™ II RTase (BRL) was added to the mixture. The incubation was continued for 60 min. at 42° C. The reaction was stopped by heating the tube for 10 min. at 95–98° C. The first strand cDNA was collected by brief centrifugation, aliquoted to new tubes, quickly frozen on dry ice, and stored at −80° C. or used immediately.

EXAMPLE 6

PCR Amplification of cDNA With a Specific Primer Set

For a 20 μl PCR reaction with radioactively labeled nucleotides, 1 μl of the cDNA prepared in accordance with the procedure of Example 5 was mixed with 20 pmol of primer 1, 20 pmol of primer 2, 2.5 μl of 2.5 mM dNTP, 5 μCi of alpha −$^{32}$p-dATP, 2 units of Taq polymerase (Boehringer-Mannheim), 0.2 μg of T4 gene 32 protein (Boehringer-Mannheim), 2 μl of 10x buffer (500 mM KCL, 100 mM Tris-HCl-pH8.3, and 20 mM MgCl$_2$), and water to a total volume of 20 μl. One drop of mineral oil was then added to the tube.

The PCR amplification conditions for the telomerase RNA component clone were: 94° C. for 45 sec., 60° C. for 45 sec., 72° C. for 1.5 min. The number of cycles differed depending on the type of purified materials used for RNA preparation but typically range from 18 to 25 cycles. As for all quantitative RT-PCR, several reactions with differing cycles were run for each sample to determine when the PCR amplification became saturated and non-linear.

For the RNase P used as a control, the PCR amplification conditions were: 94° C. for 45 sec., 50° C. for 45 sec., and 72° C. for 1.5 min. Again, the number of cycles ranged from 15 to 22 cycles, depending on the nature of the samples. The sequences of the primers used for RNase P amplification are shown below:

P3: 5'-GGAAGGTCTGAGACTAG-3' (SEQ ID NO:16)
P4: 5'-ATCTCCTGCCCAGTCTG-3' (SEQ ID NO:17)
The PCR product obtained with these two primers is about 110 bp in size.

After PCR, the products (5 to 10 μl of the reaction mixture) were loaded onto a 6% native polyacrylamide gel and electrophoresed. After electrophoresis, the gel was dried and exposed to a PhosphorImager™ cassette or to autoradiographic film for analysis.

EXAMPLE 7

Cloning the Gene for the RNA Component of Human Telomerase

The procedures used to clone the gene for the RNA component of human telomerase were carried out as generally described in Maniatis, et al., *Laboratory Molecular Cloning Manual.* A genomic DNA library of DNA from the human lung fibroblast cell line WI-38 inserted into phage lambda vector FIXII was purchased from Stratagene. The phage were plated at a concentration of about 25,000 plaques per plate onto three sets of 15 (150 mm) plates. The plates were made with NZY agar and NZY top agarose; the cells used for the phage transformation were XL1BlueMRAP2 cells; and the transformants were grown overnight for about 16 hours at 37° C. The plates were then chilled at 4° C. for about an hour, and then the plaques were "lifted" onto C/P nylon circles (filter paper from Bio Rad). This process was repeated to produce a duplicate set of lifted filters. The filters (in duplicate) were denatured, neutralized, equilibrated in 6x SSC buffer, exposed to UV irradiation to cross-link the nucleic acid to the filter, and then dried on blotter paper.

Prehybridization was conducted for one hour at 37° C. in 50% formamide buffer. The filters were probed with an ~218 bp, radioactively-labeled, NotI fragment from clone pGRN7, which has been isolated by electroelution from a 5% polyacrylamide gel after separation by electrophoresis and then nick-translated with alpha-$^{32}$p-dCTP using a nick-translation kit from Boehringer-Mannheim Biochemicals in accordance with the manufacturer's instructions. About 25 ng (~10 μCi label) of the probe were used per filter, and hybridization was conducted overnight at 37° C. in 50% formamide hybridization buffer. After hybridization, the filters were washed at room temperature six times; the first three washes were with 6x SSC containing 0.1% SDS, and the last three washes were with 6x SSC alone. After an initial exposure of several duplicate filters in a PhosphorImager™ cassette to check hybridization efficiency and signal strength, the filters were washed at 65° C. in 0.5x SSC. The filters were then placed under Kodak XAR5 film using two intensifier screens and then allowed to expose the film for about 100 hours at −70° C.

One strong signal emanated from the filter containing a phage, later designated 28-1, comprising the gene for the RNA component of human telomerase. The plaque corresponding to the signal observed on the filter was used to make secondary plates, so that an isolated plaque (confirmed by probing with labeled pGRN7 nucleic acid) could be cultured for large-scale isolation of the phage DNA. Phage 28-1, available from the American Type Culture Collection under ATCC accession No. 75925, comprises an ~15 kb insert and comprises several restriction fragments that contain sequences that hybridize with RNA component sequences on pGRN7: a 4.2 kb EcoRI restriction enzyme fragment; a 4.5 kb ClaI restriction enzyme fragment, and a 2.5 kb HindIII-SacI restriction enzyme fragment. The latter fragment comprises the entire ~560 nucleotide sequence of the RNA component shown above and is believed to comprise the complete gene for the RNA component. The plasmid comprising the 2.5 kb HindIII-SacI restriction enzyme fragment in the pBluescript vector was designated plasmid pGRN33 and is available from the American Type Culture Collection under ATCC accession No. 75926. To the extent the human gene may comprise sequences other than those on the 2.5 kb fragment, those sequences can be isolated from phage 28-1 or from other phage clones identified by probing with the 2.5 kb fragment (or another probe of the invention).

The restriction enzyme fragments noted above were prepared in separate restriction enzyme digests; the products of the digests were separated by electrophoresis on a 0.7% agarose gel or, for the ~2.5 kb fragment only, a 3% polyacrylamide gel; and the desired bands were cut from the gel and prepared for subcloning either by using the GeneClean™ Kit II (from Bio101, Inc.) or by electroelution into Spectropor #2 dialysis tubing in 0.1x TBE at 100 V for two hours (for the ~2.5 kb fragment only).

These restriction enzyme fragments were subcloned into *E. coli* expression/mutagenesis plasmids derived from pUC-based plasmids or from pBluescriptII plasmids that also comprise an SV40 origin of replication (but no SV40 promoter activity). The resulting plasmids can be used to prepare altered (mutated) RNA component nucleic acids for introduction into human or other eukaryotic cells for a variety of purposes, as described above in the Description of the Preferred Embodiments.

EXAMPLE 8

Antisense Plasmids for the RNA Component of Human Telomerase

Antisense expression plasmids were prepared by PCR amplification of RNA component cDNA using the following primer sets: (1) NotB and G1, which produces an antisense nucleic acid that is smaller than the cDNA insert in the plasmid; and (2) NotB and R3C, which produces a full-length (relative to the insert in the plasmid) antisense nucleic acid. The nucleotide sequence of NotB is shown in Example 1, above: the nucleotide sequences of the G1 and R3 primers are shown below.

G 1 :
5'-GAGAAAAACAGCGCGCGGGGAGCAAAAGCA-3'
(SEQ ID NO:18)

R3C: 5'-GTTTGCTCTAGAATGAACGGTGGAAG-3'
(SEQ ID NO:19)

After PCT amplification, the amplified fragments were cloned into an ~10 kb expression plasmid at a PmlI site: the plasmid comprises puromycin resistance-conferring, DHFR, and hygromycin B resistance-conferring genes as selectable markers, the SV40 origin of replication; the inducible human metallothionein gene promoter positioned for expression of the antisense strand of the gene for the RNA component of human telomerase (one could also use a stronger promoter to get higher expression levels), and the SV40 late poly A addition site.

The resulting plasmids (designated pGRN42 for the NotB/G1 product and pGRN45 for the NotB/R3C product) were transfected by the calcium phosphate procedure (see Maniatis, et al., supra) into the fibrosarcoma cell line HT1080. HT1080 cells are normally immortal; expression of the antisense RNA for the RNA component of human telomerase should prevent the RNA component of human telomerase from association with the protein components, blocking the formation of active telomerase and rendering the cells mortal.

EXAMPLE 9

Mouse Telomerase Activity Purification

Forty liters of mouse FM3A cells were grown in suspension in DMEM medium supplemented with 10% calf serum to a density of $0.5\ 10^5$ cells/ml. S-100 cytoplasmic extracts were prepared as described (Counter, et al. (1992) EMBO J. 11:1921–1929; Prowse, et al. (1993) supra) and glycerol and NaCl were added to a final concentration of 10% and 0.1 M, respectively. For purification of mouse telomerase activity, the S-100 extracts were passed through 30 ml of a DEAE-agarose column previously equilibrated in 1x hypo-buffer (Prowse, et al. (1993) supra) containing 0.1 M NaCl as well as several protease inhibitors. After collection, the flow through the column was washed with 3 volumes of hypo-buffer-0.1 M NaCl. Hypo-buffer containing increasing NaCl concentrations (0.2 M, 0.35 M, 0.5 M and 0.7 M) was used as eluant, and 100 ml fractions were collected at each salt concentration. Telomerase activity eluted at 0.35 M NaCl. This telomerase-containing fraction was then diluted with 1x hypo buffer to 0.1 M NaCl final concentration and loaded on a 10 ml of a spermine-agarose column previously equilibrated with 1x hypo-buffer-0.1 M NaCl. After collecting the flow through, the wash and elution steps were carried out as described previously (Prowse, et al. (1993) supra; the volume of each eluate was 20 ml and activity eluted between 0.35 M and 0.5 M NaCl. The lower salt fraction, containing most of the telomerase activity was loaded onto an octyl-sepharose column equilibrated with 1x hypo-buffer-0.1 M NaCl. The column was washed as described previously and eluted with 1x hypo-buffer containing 1% triton X-100, fractions of 3 ml were collected, most of the telomerase activity was in fraction number 3.

Twenty $\mu$l of each fraction were used to assay telomerase activity as described (Prowse, et al. (1993) supra). RNA was prepared from all the column fractions by extracting 100 $\mu$l of each fraction first with one volume of phenol and then with one volume of phenol/chloroform followed by ethanol precipitation (Sambrook, et al., (1989) Molecular Cloning—a laboratory manual, Cold Spring Harbor Laboratory, Cold Spring Harbor, N.Y.). RNA was run on a 6% acrylamide/urea gel at 20 W. RNA was electroblotted to a Hybond N+ membrane and hybridized with a 300 bp PCR fragment of mouse telomerase RNA (mTR) gene. Hybridization was done at 65° C. in 1% BSA, 200 mM NaPO₄, 15% formamide, 1 mM EDTA and 7% SDS. Filters were washed in 0.4x SSC, 0.1% SDS at 65° C.

EXAMPLE 10

Mouse Genomic Library Screening

A genomic library from D3 embryonic stem cells cloned in λ EMBL3 was used for screening. Three to four genomes were plated for the primary screening using the strain LE392 (P2) as plating cells. A PCR product of 450 bp of the human telomerase RNA (hTR) gene was gel purified and radiolabeled by hexameter labeling (Sambrook, et al. (1989) supra) using high specific activity (3000 Ci/mmol) dNTPs. The sequences of the primers used to generate the probe were as follows:
u3b: 5'-GCCTGGAGGGGTGGTGGCCATTTTTTG-3' (SEQ ID NO:20)
ol3: 5'-GATCGGCGTTCCCCCCACCAAC-3' (SEQ ID NO:21).

The mouse library was probed with the human sequence at 55° C. in a moderate stringency buffer (Sambrook, et al. (1989) supra containing 1% BSA, 500 mM NaPO₄, 15% formamide, 1 mM EDTA and 7% SDS. The filters were washed at 55° C. in 0.4x SSC and 0.1% SDS. Positive plaques were re-plated and probed again to further purify the positive lambda clones. After the isolation of single positive phage clones, 50 ml LE392(P2) culture was infected and DNA was prepared using the Qiagen Kit for lambda DNA purification. A restriction map with four different enzymes that do not cut lambda DNA sequences was done for each positive clone. Four different clones had the same pattern with each enzyme, moreover, the same size restriction fragment for each enzyme hybridized to the human probe in a Southern blot. A 5 Kb EcoRI genomic fragment containing the homology region of the human RNA was cloned into KS⁺ Bluescript vector and a further restriction map was done. The restriction enzyme PstI cut within the homology region. Both PstI fragments were cloned and sequenced.

EXAMPLE 11

RT-PCR Protocol

A 3 μg sample of total RNA from the FM3A cell line was mixed with 8 ng of random hexamers in a final volume of 10 μl, denatured at 95° C. for 10 minutes and chilled on ice. The annealing mixture was added to the reverse transcription mixture under the same conditions as for primer extension. Reverse transcriptase was not added to a control tube. Incubation was for 60 minutes at 50° C. The reactions were stopped by heating the tubes at 95° C. for 10 minutes. A 1 μl aliquot of each first strand cDNA was used for each PCR reaction. PCR reactions contained 1x PCR buffer provided with Taq polymerase, 5 mM dNTPs, 100 ng of each primer, 0.1 μg of T4 gene 32 protein and 2 units of Taq polymerase from Perkin-Elmer. The conditions of PCR amplification were: 94° C. for 1 minute; 60° C. for 45 seconds; and 72° C. for 1.5 minutes. Typically, 35 to 40 cycles were carried out for a first amplification. For nested amplification, 1 μl of the first PCR was used in a second PCR. For cloning, the PCR products were phenol extracted, precipitated and digested with restriction enzymes NotI and SalI, and cloned in KS+ Bluescript that was previously digested with NotI and SalI. Primers used were: First amplification:
mTR5b: 5'-CGTCGACTAGGGTCGAGGGCGGCTAGGCCT-3' (SEQ ID NO:22)
mTR3: 5'-GGAGGCGGCCGCAGACGTTTGATTTTTTGAGGC-3' (SEQ ID NO:23)
Second amplification:
mTR5b: (see above)
nest B: 5'-GGAGGCGGCCGCAGACGTTTGTTTTTTGAGGC-3' (SEQ ID NO:24).

EXAMPLE 12

Mouse Inhibition/Elongation Experiments

Each oligonucleotide used in these experiments was gel purified on a 10% acrylamide-urea gel; the band corresponding to the unit length size was excised and eluted from the gel in water. After elution, oligonucleotides were further purified using a NAP-5 column (Pharmacia, Inc.). The concentration of each oligonucleotide was determined by measuring the O.D. at 260 nm. For both inhibition and priming experiments, the indicated amount of oligonucleotide was preincubated on ice for 30 min. with 20 μl of a DEAE-agarose fraction containing telomerase activity, either pretreated or not with DNase-free RNase. After preincubation, 20 μl of 2x telomerase reaction mix (100 mM Tris-acetate, pH 8.5; 100 mM potassium acetate, 4 mM dTTP, 4 mM dATP, 2 mM MgCl₂, 2 mM spermidine, 2 mM EGTA, 10 mM 2-mercaptoethanol, 20 μCi of a-32P dGTP (800 Ci/mmol, New England Nuclear)) was added and telomerase reactions were carried out as described. For the inhibition studies, 1.0 μg of telomeric oligonucleotide $(T_2AG_3)_3$ was also added to the 2x reaction mix for the inhibition studies. All ddNTPs were used at a final concentration of 2 mM.

The sequence of the oligonucleotides used for inhibition and elongation experiments were as follows:
MI-2: ATGAAAATCAGGGTTAGG (SEQ ID NO:25)
MP-1: CCACAGCTAATGAAAATC (SEQ ID NO:26)
MP-4: CCACAGCTAATGAAAATCAGGGTTAGG (SEQ ID NO:27)
MI-3: TCACGTTCAAGGGTTAGG (SEQ ID NO:28)
MI-5: ATGAAAATCGCTACCTAA (SEQ ID NO:29)
MP-3: CCCACAGCTAATGAAAAT (SEQ ID NO:30)
MP-4: CCCCACAGCTAATGAAAA (SEQ ID NO:31).

EXAMPLE 13

Northern Blots of Cell Culture and Tissues

Total RNA from different mouse tissues was purchased from Clontech, and total RNA from pre-crisis and post-crisis Mus spretus fibroblasts was prepared from 90 mm tissue culture plates as described (Sambrook, et al., 1989). RNA concentration was determined measuring the absorbance at 260 nm in a spectrophotometer. Twenty μg of each RNA was run on a 6% acrylamide-7M urea gel and transferred to Hybond N+ membrane. Hybridization with the mouse telomerase RNA (mTR) probe was done in high stringency conditions as described in Sambrook, et al. (1989) supra.

EXAMPLE 14

Construction of a Mouse Knockout Plasmid

FIG. 6 shows the restriction map for approximately 15 kb surrounding the mouse telomerase RNA component gene in the mouse genome. For targeting a standard mouse knock out, vector pPNT was used (plasmid structure shown at bottom of the figure). To create the specific knockout plasmid, a 3.3 kb fragment of genomic DNA 5' region of the mouse gene was altered to add a SacI (Sc) site by site-directed mutagenesis. The 3.3 kb fragment was cloned into the XbaI site downstream from the neo gene in pPNT. In addition, a 4.0 kb genomic fragment from the 3" region flanking the mouse telomerase RNA gene was altered to add a SacI restriction site. This fragment was then cloned into the upstream XhoI site in the pPNT vector.

EXAMPLE 15

Identification and Isolation of RNA Component Nucleic Acids From Other Non-human Mammals To illustrate how the reagents of the invention can be used to identify and isolate substantially homologous nucleic acids from other mammalian species, PCR primers complementary to human RNA component sequences were used to amplify homologous sequences in a PCR. An illustrative primer pair used to demonstrate this aspect of the invention is composed of primer +10, which has the sequence 5'-CACCGGGTTGCGGAGGGAGG-3' (SEQ ID NO:32), and primer R7 which has the sequence 5'-GGAGGGGCGAACGGGCCAGCA-3' (SEQ ID NO:33). Genomic DNA was prepared from chimpanzee, squirrel monkey, rhesus monkey, and baboon tissue and dissolved in TE buffer at a concentration of about 0.5-4 mg/ml.

For each tissue type, a PCR mixture was prepared, which mixture comprised: 1 $\mu$L of genomic DNA, 48 $\mu$L of Master Mix (Master Mix is composed of 1x TaqExtender™ buffer from Stratagene, 200 $\mu$M of each dNTP, and 0.5 $\mu$M of each primer), and 0.5 $\mu$L of a 1:1 mixture of Taq polymerase (5 units/$\mu$L, Boehringer-Mannheim):Tth polymerase (TaqExtender™ polymerase, from Stratagene). The reaction tubes were loaded onto a thermal cycler, which was programmed to first heat the reaction mixture at 94° C. for 5 minutes and then to perform 27 cycles of incubations at 94° C. for 30 sec., 63° C. for 10 sec., and 72° C. for 45 sec. After the amplification reaction was complete, about 10 $\mu$L of each reaction mixture were loaded onto a 2% agarose gel for electrophoresis. After electrophoresis, staining of the gel, and UV irradiation, one could observe that each reaction mixture contained a band of the predicted (~200 bp) size. Nucleic acids from these bands can be cloned and sequenced and the remainder of the RNA component genes from each of these mammalian species can be cloned as described above for the gene for the RNA component of human telomerase or mouse telomerase.

A similar procedure was used to clone and partially sequence the RNA component of rat telomerase. PCR primers were designed to the conserved regions between the human and the mouse RNA components. In addition to mouse genomic sequence, a Sal1 restriction site was added onto the 5' primer and Not1 restriction site added onto the 3' primer to allow efficient cloning. The sequence of the primers are:

mTR 5': 5'-CGTCGACTAGCGCTGTTTTCTC-GCTGACT-3' (SEQ ID NO:34)

Mtr 3': 5'-GGAGGCGGCCGCAGGTGCACTTCCCA-CAGCTCAG (SEQ ID NO:35).

These primers were used to PCR a specific sequence of the rat telomerase RNA component. Genomic DNA was isolated using standard procedures (Sambrook, et al., supra), and a region of the rat telomerase RNA gene was amplified with these two primers using procedures described in Sambrook, et al., supra. The PCR fragment was cloned and sequenced. This sequence comprises 269 nucleotides and is shown in FIG. 7 (SEQ ID NO:5).

The sequence obtained between the PCR primers showed a 74% homology to the mouse telomerase RNA gene. Since the sequence that was amplified between the primers was not used to select this clone, the 74% homology indicates that the correct gene had been cloned. To clone the full length of the gene, a genomic library was probed with the cloned rat fragment. Five positive clones were identified when five genome equivalents were screened. This suggests that the rat gene exists as a single copy in the rat genome, like the mouse and human genes in their genomes.

Using the same primers described above, appropriate sized PCR fragments have been generated using genomic DNA from Mink, Chinese Hamster, African Green Monkey and the African horned frog Xenopus. Thus primers to conserved sequences in the human and mouse telomerase RNA genes can be generally useful in cloning telomerase RNA genes from many different mammalian species and even from other vertebrates.

The foregoing examples describe various aspects of the invention and how certain nucleic acids of the invention were made. The examples are not intended to provide an exhaustive description of the many different embodiments of the invention encompassed by the following claims.

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
      (A) LENGTH: 2425 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GATCAGTTAG AAAGTTACTA GTCCACATAT AAAGTGCCAA GTCTTGTACT CAAGATTATA    60

-continued

| | |
|---|---|
| AGCAATAGGA ATTTAAAAAA AGAAATTATG AAAACTGACA AGATTTAGTG CCTACTTAGA | 120 |
| TATGAAGGGG AAAGAAGGGT TTGAGATAAT GTGGGATGCT AAGAGAATGG TGGTAGTGTT | 180 |
| GACATATAAC TCAAAGCATT TAGCATCTAC TCTATGTAAG GTACTGTGCT AAGTGCAATA | 240 |
| GTGCTAAAAA CAGGAGTCAG ATTCTGTCCG TAAAAAACTT TACAACCTGG CAGATGCTAT | 300 |
| GAAAGAAAAA GGGGATGGGA GAGAGAGAAG GAGGGAGAGA GATGGAGAGG GAGATATTTT | 360 |
| ACTTTTCTTT CAGATCGAGG ACCGACAGCG ACAACTCCAC GGAGTTTATC TAACTGAATA | 420 |
| CGAGTAAAAC TTTTAAGATC ATCCTGTCAT TTATATGTAA AACTGCACTA TACTGGCCAT | 480 |
| TATAAAAATT CGCGGCCGGG TGCGGTGGCT CATACCTGTA ATCCCAGCAC TTTGGGAGGC | 540 |
| CGAAGCGGGT GGATCACTTG AGCCCTGGCG TTCGAGACCA GCCTGGGCAA CATGGTGAAA | 600 |
| CCCCCGTCTC TACTAAAAAC ACAAAAACTA GCTGGGCGTG GTGGCAGGCG CCTGTAATCC | 660 |
| CAGCTACTCA GGAGGCTGAG ACACGAGAAT CGCTTGAACC CGGGAGCAGA GGTTGCAGTG | 720 |
| AGCCGAGATC ACGCCACTAG ACTCCATCCA GCCTGGGCGA AAGAGCAAGA CTCCGTCTCA | 780 |
| AAAAAAAAAA TCGTTACAAT TTATGGTGGA TTACTCCCCT CTTTTTACCT CATCAAGACA | 840 |
| CAGCACTACT TTAAAGCAAA GTCAATGATT GAAACGCCTT TCTTTCCTAA TAAAAGGGAG | 900 |
| ATTCAGTCCT TAAGATTAAT AATGTAGTAG TTACACTTGA TTAAAGCCAT CCTCTGCTCA | 960 |
| AGGAGAGGCT GGAGAAGGCA TTCTAAGGAG AAGGGGGCAG GGTAGGAACT CGGACGCATC | 1020 |
| CCACTGAGCC GAGACAAGAT TCTGCTGTAG TCAGTGCTGC CTGGGAATCT ATTTTCACAA | 1080 |
| AGTTCTCCAA AAAATGTGAT GATCAAAACT AGGAATTAGT GTTCTGTGTC TTAGGCCCTA | 1140 |
| AAATCTTCCT GTGAATTCCA TTTTTAAGGT AGTCGAGGTG AACCGCGTCT GGTCTGCAGA | 1200 |
| GGATAGAAAA AAGGCCCTCT GATACCTCAA GTTAGTTTCA CCTTTAAAGA AGGTCGGAAG | 1260 |
| TAAAGACGCA AAGCCTTTCC CGGACGTGCG GAAGGGCAAC GTCCTTCCTC ATGGCCGGAA | 1320 |
| ATGGAACTTT AATTTCCCGT TCCCCCCAAC CAGCCCGCCC GAGAGAGTGA CTCTCACGAG | 1380 |
| AGCCGCGAGA GTCAGCTTGG CCAATCCGTG CGGTCGGCGG CCGCTCCCTT TATAAGCCGA | 1440 |
| CTCGCCCGGC AGCGCACCGG GTTGCGGAGG GAGGGTGGGC CTGGGAGGGG TGGTGGCCAT | 1500 |
| TTTTTGTCTA ACCCTAACTG AGAAGGGCGT AGGCGCCGTG CTTTTGCTCC CCGCGCGCTG | 1560 |
| TTTTTCTCGC TGACTTTCAG CGGGCGGAAA AGCCTCGGCC TGCCGCCTTC CACCGTTCAT | 1620 |
| TCTAGAGCAA ACAAAAAATG TCAGCTGCTG GCCCGTTCGC CCCTCCCGGG ACCTGCGGCG | 1680 |
| GGTCGCTGCC CAGCCCCCGA ACCCCGCCTG GAGGCCGCGG TCGGCCGGGG CTTCTCCGGA | 1740 |
| GGCACCCACT GCCACCGCGA AGAGTTGGGC TCTGTCAGCC GCGGGTCTCT CGGGGGCGAG | 1800 |
| GGCGAGGTTC ACCGTTTCAG GCCGCAGGAA GAGGAACGGA GCGAGTCCCG CGCGCGGCGC | 1860 |
| GATTCCCTGA GCTATGGGAC GTGCACCCAG GACTCGGCTC ACACATGCAG TTCGCTTTCC | 1920 |
| TGTTGGTGGG GGGAACGCCG ATCGTGCGCA TCCGTCACCC CTCGCCGGCA GTGGGGCTT | 1980 |
| GTGAACCCCC AAACCTGACT GACTGGGCCA GTGTGCTGCA AATTGGCAGG AGACGTGAAG | 2040 |
| GCACCTCCAA AGTCGGCCAA AATGAATGGG CAGTGAGCCG GGGTTGCCTG GAGCCGTTCC | 2100 |
| TGCGTGGGTT CTCCCGTCTT CCGCTTTTTG TTGCCTTTTA TGGTTGTATT ACAACTTAGT | 2160 |
| TCCTGCTCTG CAGATTTTGT TGAGGTTTTT GCTTCTCCCA AGGTAGATCT CGACCAGTCC | 2220 |
| CTCAACGGGG TGTGGGAGA ACAGTCATTT TTTTTTGAGA GATCATTTAA CATTTAATGA | 2280 |
| ATATTTAATT AGAAGATCTA AATGAACATT GGAAATTGTG TTCCTTTAAT GGTCATCGGT | 2340 |
| TTATGCCAGA GGTTAGAAGT TTCTTTTTTG AAAAATTAGA CCTTGGCGAT GACCTTGAGC | 2400 |
| AGTAGGATAT AACCCCCACA AGCTT | 2425 |

(2) INFORMATION FOR SEQ ID NO:2:

(i) SEQUENCE CHARACTERISTICS:
        (A) LENGTH: 559 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:2:

```
GGGUUGCGGA GGGAGGGUGG GCCUGGGAGG GGUGGUGGCC AUUUUUUGUC UAACCCUAAC    60
UGAGAAGGGC GUAGGCGCCG UGCUUUUGCU CCCCGCGCGC UGUUUUUCUC GCUGACUUUC   120
AGCGGGCGGA AAAGCCUCGG CCUGCCGCCU UCCACCGUUC AUUCUAGAGC AAACAAAAAA   180
UGUCAGCUGC UGGCCCGUUC GCCCCUCCCG GGACCUGCGG CGGGUCGCUG CCCAGCCCCC   240
GAACCCCGCC UGGAGGCCGC GGUCGGCCGG GGCUUCUCCG GAGGCACCCA CUGCCACCGC   300
GAAGAGUUGG GCUCUGUCAG CCGCGGGUCU CUCGGGGGCG AGGGCGAGGU UCACCGUUUC   360
AGGCCGCAGG AAGAGGAACG GAGCGAGUCC CGCGCGCGGC GCGAUUCCCU GAGCUAUGGG   420
ACGUGCACCC AGGACUCGGC UCACACAUGC AGUUCGCUUU CCUGUUGGUG GGGGAACGC    480
CGAUCGUGCG CAUCCGUCAC CCCUCGCCGG CAGUGGGGGC UUGUGAACCC CCAAACCUGA   540
CUGACUGGGC CAGUGUGCU                                                559
```

(2) INFORMATION FOR SEQ ID NO:3:

(i) SEQUENCE CHARACTERISTICS:
        (A) LENGTH: 1259 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
TTTTTTTTTT CCTCGTAATC TTTTTTTTTG TTTTAAACAC TGGAACTTGA TGTCTGGAGG    60
ACGGAGTCGG AGGATGTTCG ACCCTAATAT CCGAGCCCAG TCGATGGGAA CTTTAAGAAA   120
AAGAAAGACC TTGAGTCATG GACCAACCGG TACGTGAGTG TTCTCTAGGC GGACGGAAGA   180
CAGTTTAAGA CCTTAATTTC TAAACGCGGT GAAAAGGGGT GAAGGTGGGG GCCGACACCC   240
TCACCTGACC CAACTTCCAC CTTAAAAAAA AAAAAAAAA AATCACTTTT TTCCCCCCTA    300
ACCTTTATAG GGGATGAAAT ATCCTACTTT CAACTCTAGT ATATTTCAGA AACCAAGCCT   360
CAGAGATGTG CGTGCGTGCG TGTGTGTGTG TGTATGTGTG TGTGTCTCAC AGCAAGAAAC   420
AGATTTTATT ATTTATTTTT TATTTATTTA TTTTTTGCAA GTGACTGGCT AGGAAGAGTG   480
GGGAAGCGGG AGGACAAATG GGAAGAGGG AGCATTTCCG CAAGTGCTGG GCTCGACCAA    540
TCAGCGCGAG CCATGGGGTA TTTAAGGTCG AGGGCGGCTA GGCCTCGGCA CCTAACCCTG   600
ATTTTCATTA GCTGTGGGTT CTGGTCTTTT GTTCTCCGCC CGCTGTTTTT CTCGCTGACT   660
TCCAGCGGGC CAGGAAAGTC CAGACCTGCA GCGGGCCACC CGGCGTTCCC GAGCCTCAAA   720
AACAAACGTC AGCGCAGGAG CTCCAGGTTC GCCGGGAGCT CCGCGCGCCG GCCGCCAGT    780
CCCGTACCCG CCTACAGGCC GCGGCGCTGG GGTCTTAGGA CTCCGCTGCC GCCGCGAAGA   840
GCTGCGCTCT GTCAGCCGCG GGCGCGCGGG GCGTGGGGCA GGCGGGCGAG CGCGCGAGGA   900
CAGGAATGGA ACTGGTCCGT GTTCGGTGTC TTACTGAGCT GTGGGAAGTG CACCGGACTC   960
GGTTCTCACA CCCCATTCCC GCTGGGGAAA TGCCCCGCTG CAGGGCGGGC CGCTAGAACC  1020
```

```
TGCGACTCTG GGGAAAGGGG CTTCGGTGTG AGACGGTAGC CAGCCAAAGG GTATATATCG   1080

CCCTCACGCC CCGTCCCCCT CCACTTTTGT CTAATACTCC TGTTTCTGTT GTGCAGATTT   1140

TGCAGGCGTT TCGCTGGCTC TGCCTGAACG AGCTATCAGC CATGTGGTCC TTGGGGGTGG   1200

GGGTGGGGAT GGGTTGTGTA GTGCTGGAA TGAACCTAGT TTCTAAGTTC TCTATCAAC    1259

(2) INFORMATION FOR SEQ ID NO:4:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:4:

CUCGACCAAU CAGCGCGAGC CAUGGGGUAU UUAAGGUCGA GGGCGGCUAG GCCUCGGCAC     60

CUAACCCUGA UUUUCAUUAG CUGUGGGUUC UGGUCUUUUG UUCUCCGCCC GCUGUUUUUC    120

UCGCUGACUU CCAGCGGGCC AGGAAAGUCC AGACCUGCAG CGGGCCACCC GGCGUUCCCG    180

AGCCUCAAAA ACAAACGUCA GCGCAGGAGC UCCAGGUUCG CCGGGAGCUC CGCGCGCCGG    240

GCCGCCAGUC CCGUACCCGC CUACAGGCCG CGGCGCUGGG GUCUUAGGAC UCCGCUGCCG    300

CCGCGAAGAG CUGCGCUCUG UCAGCCGCGG GCGCGCGGGG CGUGGGGCAG GCGGGCGAGC    360

GCGCGAGGAC AGGAAUGGAA CUGGUCCGUG UUCGGUGUCU UACUGAGCUG UGGGAAGUGC    420

ACCGGACUCG GUUCUCACAC CCCAUUCCCG CUGGGGAAAU GCCCCGCUGC AGGGCGGGCC    480

GCUAGAACCU GCGACUCUGG GGAAAGGGGC UUCGGUGUGA GACGGUAGCC AGCC          534

(2) INFORMATION FOR SEQ ID NO:5:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:5:

UCAGCGGGCC UGAAAGUUCA GACCUGCAGC GGGUCACGCG CAUUCUGAAC CUCAAAAAAU     60

GUCAGCGUAG AGCUCUGGUG CCAGAGCUCG NCGGCGCUGG GCCGCCCAGC CCGGUACCCN    120

GCCUGGAGCC GCGGACGGCC UGGGGUCUUA GAACCGUGCC GCCGUGAAGA GCUAGUUUCU    180

GUUAGCUACG GGGCACCGGG CGCUGGGGUC AGGCCGGGAG AGCGCCGCAA GGACAGUAAC    240

GGAACUGGUC CCUGAGUUCG GUGGCUUUC                                      269

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

CUCAGUUAGG GUUAGACAAA                                                  20

(2) INFORMATION FOR SEQ ID NO:7:

(i) SEQUENCE CHARACTERISTICS:
```

(A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:7:

CGCCCUUCUC AGUUAGGGUU AG                                        22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:8:

GGCGCCUACG CCCUUCUCAG UU                                        22

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

CAGGCCCACC CTCCGCAACC                                           20

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:10:

UAGGGUUACU GAUGAGUCCG UGAGGACGAA ACAAAAAAU                       39

(2) INFORMATION FOR SEQ ID NO:11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:11:

UUAGGGUCUG AUGAGUCCGU GAGGACGAAA GACAAAA                         37

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:12:

UCUCAGUCUG AUGAGUCCGU GAGGACGAAA GGGUUA                          36

(2) INFORMATION FOR SEQ ID NO:13:

(i) SEQUENCE CHARACTERISTICS:
        (A) LENGTH: 36 base pairs
        (B) TYPE: nucleic acid

```
            (C) STRANDEDNESS: single
            (D) TOPOLOGY: linear (xi) SEQUENCE DESCRIPTION: SEQ ID NO:13:

CCCGAGACUG AUGAGUCCGU GAGGACGAAA CCCGCG                                  36

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 20
            (D) OTHER INFORMATION: /note= "Amino blocking group linked
                at this position."

(xi) SEQUENCE DESCRIPTION: SEQ ID NO:14:

ATAGCGGCCG CAAGAATTCA                                                    20

(2) INFORMATION FOR SEQ ID NO:15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:15:

TGAATTCTTG CGGCCGCTAT                                                    20

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:16:

GGAAGGTCTG AGACTAG                                                       17

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:17:

ATCTCCTGCC CAGTCTG                                                       17

(2) INFORMATION FOR SEQ ID NO:18:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:18:

GAGAAAAACA GCGCGCGGGG AGCAAAAGCA                                         30

(2) INFORMATION FOR SEQ ID NO:19:
```

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:19:

GTTTGCTCTA GAATGAACGG TGGAAG                                              26

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:20:

GCCTGGAGGG GTGGTGGCCA TTTTTTG                                             27

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

GATCGGCGTT CCCCCCACCA AC                                                  22

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:22:

CGTCGACTAG GGTCGAGGGC GGCTAGGCCT                                          30

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:23:

GGAGGCGGCC GCAGACGTTT GATTTTTGA GGC                                       33

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:24:

GGAGGCGGCC GCAGACGTTT GTTTTTTGAG GC                                       32

(2) INFORMATION FOR SEQ ID NO:25:

(i) SEQUENCE CHARACTERISTICS:

(A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:25:

ATGAAAATCA GGGTTAGG                                                       18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:26:

CCACAGCTAA TGAAAATC                                                       18

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:27:

CCACAGCTAA TGAAAATCAG GGTTAGG                                             27

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:28:

TCACGTTCAA GGGTTAGG                                                       18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:29:

ATGAAAATCG CTACCTAA                                                       18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:30:

CCCACAGCTA ATGAAAAT                                                       18

(2) INFORMATION FOR SEQ ID NO:31:

(i) SEQUENCE CHARACTERISTICS:
        (A) LENGTH: 18 base pairs
        (B) TYPE: nucleic acid

```
            (C) STRANDEDNESS: single
            (D) TOPOLOGY: linear (xi) SEQUENCE DESCRIPTION: SEQ ID NO:31:

CCCCACAGCT AATGAAAA                                                        18

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:32:

CACCGGGTTG CGGAGGGAGG                                                      20

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:33:

GGAGGGGCGA ACGGGCCAGC A                                                    21

(2) INFORMATION FOR SEQ ID NO:34:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:34:

CGTCGACTAG CGCTGTTTTT CTCGCTGACT                                           30

(2) INFORMATION FOR SEQ ID NO:35:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:35:

GGAGGCGGCC GCAGGTGCAC TTCCCACAGC TCAG                                      34

(2) INFORMATION FOR SEQ ID NO:36:

(i) SEQUENCE CHARACTERISTICS:
            (A) LENGTH: 11 base pairs
            (B) TYPE: nucleic acid
            (C) STRANDEDNESS: double
            (D) TOPOLOGY: linear (xi) SEQUENCE DESCRIPTION: SEQ ID NO:36:

CUAACCCUAA C                                                               11

(2) INFORMATION FOR SEQ ID NO:37:

(i) SEQUENCE CHARACTERISTICS:
            (A) LENGTH: 12 base pairs
            (B) TYPE: nucleic acid
            (C) STRANDEDNESS: single
            (D) TOPOLOGY: linear
```

```
     (ix) FEATURE:
           (A) NAME/KEY: modified_base
           (B) LOCATION: 11
           (D) OTHER INFORMATION: /mod_base= i (ix) FEATURE:
           (A) NAME/KEY: modified_base
           (B) LOCATION: 12
           (D) OTHER INFORMATION: /mod_base= i
               /note= "Inosine is linked with biotin"

(xi) SEQUENCE DESCRIPTION: SEQ ID NO:37:

UUAGGGUUAG NN                                                          12

(2) INFORMATION FOR SEQ ID NO:38:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ix) FEATURE:
           (A) NAME/KEY: modified_base
           (B) LOCATION: 11
           (D) OTHER INFORMATION: /mod_base= i (ix) FEATURE:
           (A) NAME/KEY: modified_base
           (B) LOCATION: 12
           (D) OTHER INFORMATION: /mod_base= i
               /note= "Inosine is linked with biotin"

(xi) SEQUENCE DESCRIPTION: SEQ ID NO:38:

AUUGGGUUAU NN                                                          12

(2) INFORMATION FOR SEQ ID NO:39:

(i) SEQUENCE CHARACTERISTICS:
           (A) LENGTH: 9 base pairs
           (B) TYPE: nucleic acid
           (C) STRANDEDNESS: single
           (D) TOPOLOGY: linear (xi) SEQUENCE DESCRIPTION: SEQ ID NO:39:

CTAACCCTA                                                               9

(2) INFORMATION FOR SEQ ID NO:40:

(i) SEQUENCE CHARACTERISTICS:
           (A) LENGTH: 9 base pairs
           (B) TYPE: nucleic acid
           (C) STRANDEDNESS: single
           (D) TOPOLOGY: linear (xi) SEQUENCE DESCRIPTION: SEQ ID NO:40:

CAAACCCAA                                                               9

(2) INFORMATION FOR SEQ ID NO:41:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (xi) SEQUENCE DESCRIPTION: SEQ ID NO:41:

CCAACCCCAA                                                             10
```

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:42:

```
CTCACCCTCA                                                            10
```

(2) INFORMATION FOR SEQ ID NO:43:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (xi) SEQUENCE DESCRIPTION: SEQ ID NO:43:

```
CUCGACCAAU CAGCGCGCGC CAUGGGGUAU UUAAGGUCGA GGGCGGCUAG GCCUCGGCAC       60

CUAACCCUGA UUUUCAUUAG CUGUGGGUUC UGGUCUUUUG UUCUCCGCCC GCUGUUUUUC      120

UCGCUGACUU CCAGCGGGCC AGGAAAGUCC AGACCUGCAG CGGGCCACCC GGCGUUCCCG      180

AGCCUCAAAA ACAAACGUCA GCGCAGGAGC UCCAGGUUCG CCGGGAGCUC CGCGGCGCCG      240

GGCCGCCCAG UCCCGUACCC GCCUACAGGC CGCGGCCGGC CUGGGGUCUU AGGACUCCGC      300

UGCCGCCGCG AAGAGCUCCG CCUCUGUCAG CCGCGGGCGC GCGGGGGCUG GGCCAGGCC       360

GGGCGAGCGC CGCGAGGACA GGAAUGGAAC UGGUCCCCGU GUUCGGUGUC UUACCUGAGC      420

UGUGGGAAGU GCACCCGGAA CUCGGUUCUC ACAACCCCCA UUCCCGCUGG GGAAAUGCCC      480

CGCUGCAGGG CGGGCCGCUA GAACCUGCGA CUCUGGGGAA AGGGGCUUCG GUGUGAGACG      540

GUAGCCAGCC AAAGGGUAUA UAUCGCCCUC ACGCCCCGUC                            580
```

(2) INFORMATION FOR SEQ ID NO:44:

(i) SEQUENCE CHARACTERISTICS:
        (A) LENGTH: 965 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
GGGTTGCGGA GGGTGGGCCT GGGAGGGGTG GTGGCCATTT TTTGTCTAAC CCTAACTGAG       60

AAGGGCGTAG GCGCCGTGCT TTTGCTCCCC GCGCGCTGTT TTTCTCGCTG ACTTTCAGCG      120

GGCGGAAAAG CCTCGGCCTG CCGCCTTCCA CCGTTCATTC TAGAGCAAAC AAAAAATGTC      180

AGCTGCTGGC CCGTTCGCCT CCCGGGGACC TGCGGCGGGT CGCCTGCCCA GCCCCCGAAC      240

CCCGCCTGGA GGCCGCGGTC GGCCCGGGGC TTCTCCGGAG GCACCCACTG CCACCGCGAA      300

GAGTTGGGCT CTGTCAGCCG CGGGTCTCTC GGGGGCGAGG GCGAGGTTCA CCGTTTCAGG      360

CCGCAGGAAG AGGAACGGAG CGAGTCCCCG CGCGCGGCGC GATTCCCTGA GCTGTGGGAC      420

GTGCACCCAG GACTCGGCTC ACACATGCAG TTCGCTTTCC TGTTGGTGGG GGAACGCCG       480

ATCGTGCGCA TCCGTCACCC CTCGCCGGCA GTGGGGCTT GTGAACCCCC AAACCTGACT      540

GACTGGGCCA GTGTGCTGCA AATTGGCAGG AGACGTGAAG GCACCTCCAA AGTCGGCCAA      600

AATGAATGGG CAGTGAGCCG GGGTTGCCTG GAGCCGTTCC TGCGTGGGTT CTCCCGTCTT      660

CCGCTTTTTG TTGCCTTTTA TGGTTGTATT ACAACTTAGT TCCTGCTCTG CAGATTTTGT      720
```

| | | |
|---|---|---|
| TGAGGTTTTT GCTTCTCCCA AGGTAGATCT CGACCAGTCC CTCAACGGGG TGTGGGGAGA | | 780 |
| ACAGTCATTT TTTTTTGAGA GATCATTTAA CATTTAATGA ATATTTAATT AGAAGATCTA | | 840 |
| AATGAACATT GGAAATTGTG TTCCTTTAAT GGTCATCGGT TTATGCCAGA GGTTAGAAGT | | 900 |
| TTCTTTTTTG AAAAATTAGA CCTTGGCGAT GACCTTGAGC AGTAGGATAT AACCCCCACA | | 960 |
| AGCTT | | 965 |

(2) INFORMATION FOR SEQ ID NO:45:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:45:

| | | |
|---|---|---|
| GGGUUGCGGA GGGUGGGCCU GGGAGGGGUG GUGGCCAUUU UUUGUCUAAC CCUAACUGAG | | 60 |
| AAGGGCGUAG CGCCGUGCU UUUGCUCCCC GCGCGCUGUU UUUCUCGCUG ACUUUCAGCG | | 120 |
| GGCGGAAAAG CCUCGGCCUG CCGCCUUCCA CCGUUCAUUC UAGAGCAAAC AAAAAAUGUC | | 180 |
| AGCUGCUGGC CCGUUCGCCU CCCGGGGACC UGCGGCGGGU CGCCUGCCCA GCCCCCGAAC | | 240 |
| CCCGCCUGGA GGCCGCGGUC GGCCCGGGGC UUCUCCGGAG GCACCCACUG CCACCGCGAA | | 300 |
| GAGUUGGGCU CUGUCAGCCG CGGGUCUCUC GGGGGCGAGG GCGAGGUUCA CCGUUUCAGG | | 360 |
| CCGCAGGAAG AGGAACGGAG CGAGUCCCCG CGCGCGGCGC GAUUCCCUGA GCUGUGGGAC | | 420 |
| GUGCACCCAG GACUCGGCUC ACACAUGC | | 448 |

(2) INFORMATION FOR SEQ ID NO:46:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

| | | |
|---|---|---|
| CTCGACCAAT CAGCGCGCGC CATGGGGTAT TTAAGGTCGA GGGCGGCTAG GCCTCGGCAC | | 60 |
| CTAACCCTGA TTTTCATTAG CTGTGGGTTC TGGTCTTTTG TTCTCCGCCC GCTGTTTTTC | | 120 |
| TCGCTGACTT CCAGCGGGCC AGGAAAGTCC AGACCTGCAG CGGGCCACCC GGCGTTCCCG | | 180 |
| AGCCTCAAAA ACAAACGTCA GCGCAGGAGC TCCAGGTTCG CCGGGAGCTC CGCGGCGCCG | | 240 |
| GGCCGCCCAG TCCCGTACCC GCCTACAGGC CGCGGCCGGC CTGGGGTCTT AGGACTCCGC | | 300 |
| TGCCGCCGCG AAGAGCTCCG CCTCTGTCAG CCGCGGGCGC GCGGGGCTG GGGCCAGGCC | | 360 |
| GGGCGAGCGC CGCGAGGACA GGAATGGAAC TGGTCCCCGT GTTCGGTGTC TTACCTGAGC | | 420 |
| TGTGGGAAGT GCACCCGGAA CTCGGTTCTC ACAACCCCCA TTCCCGCTGG GGAAATGCCC | | 480 |
| CGCTGCAGGG CGGGCCGCTA GAACCTGCGA CTCTGGGGAA AGGGGCTTCG GTGTGAGACG | | 540 |
| GTAGCCAGCC AAAGGGTATA | | 560 |

(2) INFORMATION FOR SEQ ID NO:47:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:47:

| | | | | | | |
|---|---|---|---|---|---|---|
| GGGUAUUUAA | GGUCGAGGGC | GGCUAGGCCU | CGGCACCUAA | CCCUGAUUUU | CAUUAGCUGU | 60 |
| GGGUUCUGGU | CUUUUGUUCU | CCGCCCGCUG | UUUUUCUCGC | UGACUUCCAG | CGGGCCAGGA | 120 |
| AAGUCCAGAC | CUGCAGCGGG | CCACCCGGCG | UUCCCGAGCC | UCAAAAACAA | ACGUCAGCGC | 180 |
| AGGAGCUCCA | GGUUCGCCGG | GAGCUCCGCG | GCGCCGGGCC | GCCCAGUCCC | GUACCCGCCU | 240 |
| ACAGGCCGCG | GCCGGCCUGG | GGUCUUAGGA | CUCCGCUGCC | GCCGCGAAGA | GCUCCGCCUC | 300 |
| UGUCAGCCGC | GGGCGCGCGG | GGGCUGGGGC | CAGGCCGGGC | GAGCGCCGCG | AGGACAGGAA | 360 |
| UGGAACUGGU | CCCCGUGUUC | GGUGUCUUAC | CUGAGCUGUG | GGAAGUGCAC | CCGGAACUCG | 420 |
| GUUCUCACA | | | | | | 429 |

We claim:

1. Isolated RNA comprising the RNA component of mouse telomerase, said RNA component having a sequence identical to SEQ ID NO:4 or SEQ ID NO:47.

2. An oligonucleotide comprising a sequence identical or exactly complementary to a contiguous sequence 25 to 500 nucleotides in length of the RNA component of claim 1.

3. The oligonucleotide of claim 2 that is an oligodeoxyribonucleotide.

4. The oligonucleotide of claim 2 that is an oligoribonucleotide.

5. An oligonucleotide of claim 2 containing consecutive nucleotides "CTAACCCT", that, when bound to an RNA component of mouse telomerase, inhibits or blocks the activity of the telomerase.

6. A recombinant expression plasmid comprising the oligonucleotide of claim 2 and further comprising a promoter positioned to drive transcription of an RNA complementary or identical in sequence to said oligonucleotide.

7. The recombinant expression plasmid of claim 6, wherein said plasmid functions to produce the oligonucleotide in eukaryotic host cells.

8. The recombinant expression plasmid of claim 6, wherein said plasmid functions to produce the oligonucleotide in prokaryotic host cells.

9. The recombinant expression plasmid of claim 7, wherein said plasmid comprises a mouse gene for the RNA component of mouse telomerase.

10. The recombinant expression plasmid of claim 9, wherein said gene comprises a nucleotide sequence according to SEQ ID NO:3 or SEQ ID NO:46.

11. A eukaryotic host cell transformed with a recombinant expression plasmid of claim 6 that expresses an RNA molecule that associates with protein components of mouse telomerase to produce telomerase activity capable of adding sequences of repeating units of nucleotides to telomeres.

12. The host cell of claim 11, wherein said repeating unit is 5'-TTAGG-3'.

13. The host cell of claim 11, wherein said repeating unit is not 5'-TTAGG-3'.

14. The host cell of claim 11, wherein said RNA molecule comprises SEQ ID NO:4 or SEQ ID NO:47.

15. The host cell of claim 11, wherein said recombinant expression vector comprises a sequence of nucleotides having at least 20 or more contiguous nucleotides identical to the sequence of SEQ ID NO:3 or SEQ ID NO:46.

16. A coding region of an RNA component of a nonhuman mammalian telomerase that comprises a sequence that hybridizes to a sequence in the RNA component of claim 1 at 55° C. in a buffer comprising 1% BSA, 500 mM NaPO$_4$, 15% formamide, 1 mM EDTA and 7% SDS.

17. A method for producing a recombinant telomerase enzyme, said method comprising transforming a eukaryotic host cell that expresses protein components of telomerase with a recombinant expression vector that expresses a nonhuman RNA component of claim 16, and culturing said host cells transformed with said vector under conditions such that the protein components and RNA component are expressed and assemble to form an active telomerase molecule which can add sequences to telomeres of chromosomal DNA.

18. Isolated RNA comprising the RNA component of a nonhuman mammalian telomerase that comprises a sequence that hybridizes to SEQ ID NO:4 or SEQ ID NO:47 at 55° C. in a buffer comprising 1% BSA, 500 mM NaPO$_4$, 15% formamide, 1 mM EDTA and 7% SDS.

19. Isolated DNA comprising the gene for the RNA component of claim 18.

20. A recombinant expression plasmid comprising the DNA of claim 19 and further comprising a promoter positioned to drive transcription of an RNA complementary or identical in sequence to said DNA.

21. The recombinant expression plasmid of claim 20, wherein said plasmid functions to produce the oligonucleotide in a host cell.

22. A eukaryotic host cell transformed with a recombinant expression plasmid of claim 20 that expresses an RNA molecule that associates with protein components of a telomerase to produce telomerase activity which can add sequences of repeating units of nucleotides to telomeres.

23. An isolated RNA component of rat telomerase.

24. DNA probes or primers comprising a consecutive nonhuman sequence of about 25 to 200 or more eoxyribonucleotides encompassing conserved sequences between SEQ ID NO:44 and SEQ ID NO:46.

25. RNA probes or primers comprising a consecutive sequence of about 25 to 200 or more ribonucleotides encompassing conserved sequences between SEQ ID NO:45 and SEQ ID NO:47.

26. Isolated nonhuman DNA sequences that hybridize at 55° C. in a buffer comprising 1% BSA, 500 mM NaPO$_4$, 15% formamide, 1 mM EDTA and 7% SDS to the conserved sequences of claim 24.

27. An isolated nonhuman RNA sequence that hybridizes at 55° C. in a buffer comprising 1% BSA, 500 mM NaPO$_4$, 15% formamide, 1 mM EDTA and 7% SDS to the conserved sequences between SEQ ID NO:1 and SEQ ID NO:3.

28. A plasmid comprising a portion of the mouse genome wherein the telomerase RNA component gene is replaced with a different DNA sequence.

29. An isolated oligonucleotide according to claim 2 wherein the contiguous sequence is 50 or more contiguous nucleotides in length.

30. An isolated oligonucleotide according to claim 2 wherein the contiguous sequence is 200 or more contiguous nucleotides in length.

31. A cell comprising a portion of the mouse genome wherein the telomerase RNA component gene is replaced with a different DNA sequence.

* * * * *

UNITED STATES PATENT AND TRADEMARK OFFICE
CERTIFICATE OF CORRECTION

PATENT NO. : 6,013,468
DATED : January 11, 2000
INVENTOR(S) : William H. Andrews, Ariel Athena Avilion, Junli Feng, Walter Funk, Carol Greider, Maria Antonia Blasco Marhuenda, Bryant Villeponteau It is certified that error appears in the above-identified patent and that said Letters Patent is hereby corrected as shown below:

Title page under [73] Assignee: please insert the following:
--Geron Corporation. Menlo Park, California--

At Claim 24, Col. 56, line 61, reads "eoxyribo-" and should read --deoxyribo- --

Signed and Sealed this

Thirtieth Day of January, 2001

Attest:

Q. TODD DICKINSON

Attesting Officer

Director of Patents and Trademarks